US008561613B2

(12) United States Patent
Brambilla et al.

(10) Patent No.: US 8,561,613 B2
(45) Date of Patent: Oct. 22, 2013

(54) RESPIRATORY MASK ASSEMBLY FOR STABILIZING PATIENT INTERFACE

(75) Inventors: Enrico Brambilla, Drummoyne (AU); Renee Frances Doherty, Coogee (AU); Philip John Gunning, North Rocks (AU)

(73) Assignee: ResMed Limited, Bella Vista (AU)

( * ) Notice: Subject to any disclaimer, the term of this patent is extended or adjusted under 35 U.S.C. 154(b) by 1401 days.

(21) Appl. No.: 12/255,118

(22) Filed: Oct. 21, 2008

(65) Prior Publication Data

US 2009/0107508 A1    Apr. 30, 2009

Related U.S. Application Data

(60) Provisional application No. 60/984,133, filed on Oct. 31, 2007.

(51) Int. Cl.
*A62B 18/08* (2006.01)

(52) U.S. Cl.
USPC ............ 128/207.11; 128/204.18; 128/206.21; 128/207.13; 128/205.25

(58) Field of Classification Search
USPC .................... 128/207.11, 201.22–24, 201.29, 128/204.18, 205.25, 206.12, 206.21, 207.13
See application file for complete search history.

(56) References Cited

U.S. PATENT DOCUMENTS

| 5,724,965 | A | 3/1998 | Handke et al. | |
|---|---|---|---|---|
| 6,119,694 | A | 9/2000 | Correa et al. | |
| 2003/0196655 | A1 | 10/2003 | Ging et al. | |
| 2004/0025882 | A1 | 2/2004 | Madaus et al. | |
| 2004/0226566 | A1 | 11/2004 | Gunaratnam et al. | |
| 2005/0241644 | A1* | 11/2005 | Gunaratnam et al. | ... 128/207.18 |
| 2006/0032504 | A1* | 2/2006 | Burton et al. | ............ 128/207.11 |
| 2007/0017525 | A1 | 1/2007 | Madaus et al. | |
| 2007/0209663 | A1* | 9/2007 | Marque et al. | ........... 128/207.11 |
| 2010/0000537 | A1* | 1/2010 | McAuley et al. | ........ 128/205.25 |
| 2010/0258132 | A1* | 10/2010 | Moore | ..................... 128/207.11 |

FOREIGN PATENT DOCUMENTS

EP    1 305 070 B1    12/2005
WO    WO 2008/007985 A1    1/2008

* cited by examiner

*Primary Examiner* — Justine Yu
*Assistant Examiner* — Colin W Stuart
(74) *Attorney, Agent, or Firm* — Nixon & Vanderhye P.C.

(57) ABSTRACT

A respiratory mask assembly for delivering a flow of pressurized breathable gas to a patient includes a structure configured to contact a) at least one point on the patient's forehead, b) two points on the patient's temples, the two temple points being on opposite sides of the patient's face, and c) two points on the patient's cheek, the two cheek points being on opposite sides of the patient's face; a frame, being part of the structure, rigidly connected to other elements of the structure and configured to support a cushion in contact with the patient's face; and a plurality of straps connected to the other elements of the structure and configured to hold the frame against the at least one forehead point, the two temple points, and the two cheek points in a fully constrained manner.

64 Claims, 24 Drawing Sheets

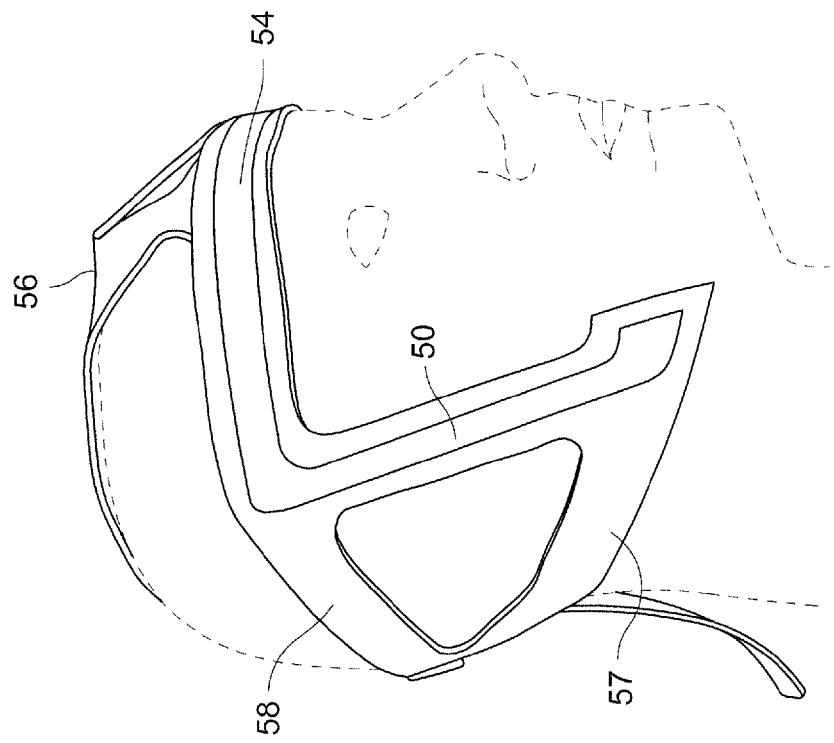
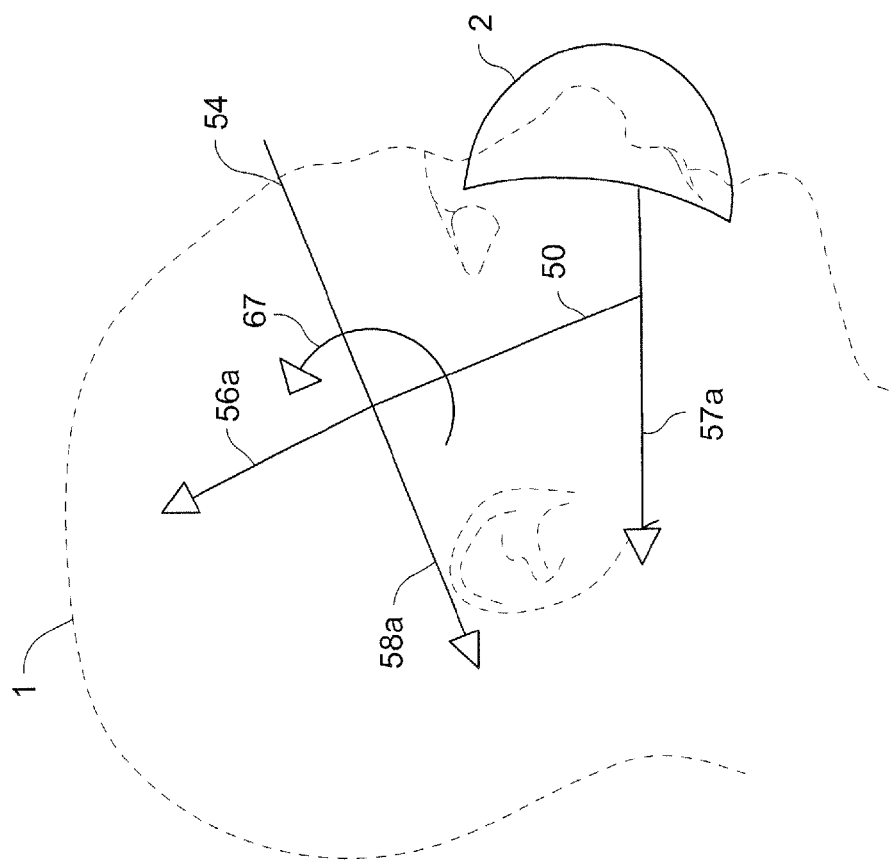
Fig. 11b
Fig. 11a

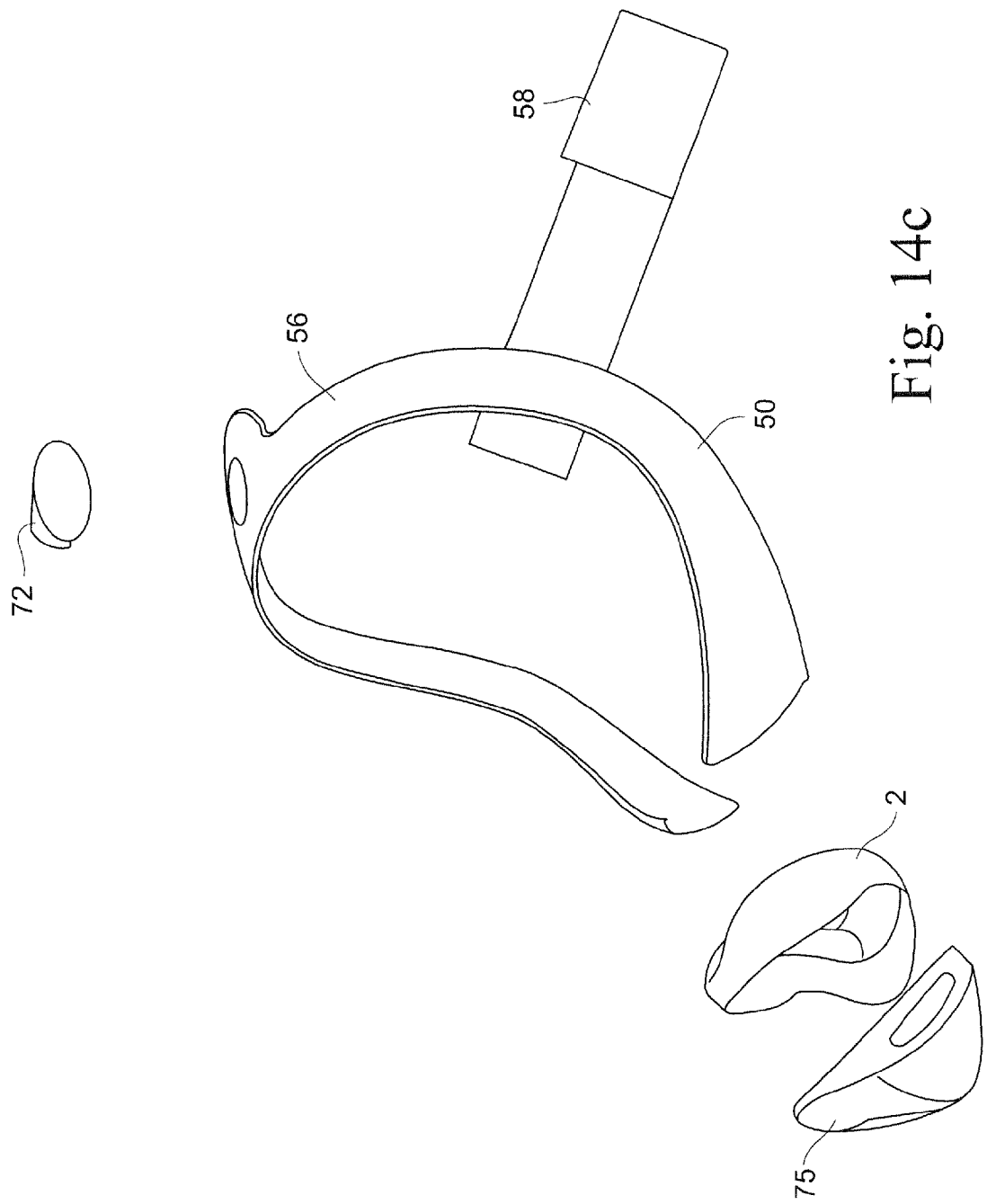

RESPIRATORY MASK ASSEMBLY FOR STABILIZING PATIENT INTERFACE

INCORPORATION BY REFERENCE

This application claims priority to U.S. Application 60/984,133, filed Oct. 31, 2007, the entire contents of which is incorporated herein by reference.

FIELD OF THE INVENTION

The present invention relates to a respiratory mask assembly for delivering a flow of breathable gas that stabilizes a patient interface configured to contact the patient's face.

BACKGROUND OF THE INVENTION

A patient interface, for example, a mask, is used to deliver positive pressure to a patient's airway to treat breathing disorders, such as sleep apnea. The patient interface is typically held against the patient's face in sealing contact by a head gear. Referring to FIG. 1, a model of a current patient interface and headgear system is shown. The patient 1 has a patient interface 2 in sealing contact with the face. A headgear may be provided to maintain the patient interface 2 in sealing contact with the face of the patient 1. The patient interface 2 may include a cushion, which is a deformable component. Forces 4 applied by straps of the headgear create a moment 6 perpendicular to the plane of the page.

As shown in FIG. 2, another current patient interface system is shown. The patient 1 has a patient interface 2 in sealing contact with the face. The patient interface 2 may be a mask that includes a forehead support that contacts the face of the patient 1 at a point 10 that may be a pivot point. Forces applied by the straps of the headgear create a moment 6 perpendicular to the plane of the page.

In the patient interface system shown in FIGS. 1 and 2, the moment 6 may make the patient interface 2 unstable on the face of the patient 1 under certain conditions. The patient interface systems shown in FIGS. 1 and 2 rely on the stiffness and deformation of the cushion of the patient interface 2 for correct location of the patient interface 2 on the face of the patient 1.

Referring to FIGS. 3a-3c, another current patient interface system is shown. The system shown in FIGS. 3a-3c is the Breeze™ manufactured by Puritan-Bennet. As shown in FIG. 3b, a headgear 11 maintains a patient interface 2 in contact with the face of the patient 1. The headgear 11 includes a pad 12a that contacts a top of the patient's head and a pad 12b that contacts the back of the patient's head. The two pads can be modeled as sliders and they identify a center of rotation 14. The reaction forces of the pads 12a, 12b can be reduced to a force vector 16 applied at the center of rotation 14 and a moment 18. Translation along the direction of the force vector 16 and rotation about the center 14 are still possible for the headgear 11. Forces 20 and 22 produced by the deformation of the patient interface 2 may balance. The headgear 11 also includes two symmetrical straps 11a (only one shown) on the sides of the head of the patient 1 that help give stability to the mask in respect to rotations around an axis laying on the plane of the page. As shown in FIGS. 3b and 3c, when the patient interface is removed from contact with the patient, as shown in FIG. 3c, the headgear 11 has a tendency to pop off the head of the patient when the reaction forces supplied by the patient interface are not present.

Referring to FIGS. 4a-4c, a patient interface system according to another known system is illustrated. The system illustrated in FIGS. 4a-4c is the Comfortlite2™ manufactured by Respironics Inc. A headgear 24 is provided to maintain contact between the patient interface 2 and the face of the patient 1. The headgear 24 includes straps 28 that apply forces that define a moment 30 around a center of rotation 29. The moment 30 tends to cause the headgear 24 to rotate about the points of contact 31, 32 with the patient's face. Any force applied to the headgear along the plane 34 (e.g. on the tube or conduit 26) can only be balanced by the reaction of the cushion of the patient interface 2. The forces given by deformation of the patient interface 2 are needed to keep the mask assembly stable on the head of the patient 1.

SUMMARY OF THE INVENTION

One aspect of the invention relates to a respiratory mask assembly to support a patient interface (e.g. a cushion, nasal pillows or prongs, etc.) that is stable on the patient's face against forces that tend to move the respiratory mask away from the patient's face.

Another aspect of the invention relates to a respiratory mask assembly that does not rely on cushion stiffness and deformation to maintain the correct position of the cushion on the patient's face.

Still another aspect of the invention relates to a respiratory mask assembly that is fully constrained to the patient's head even when the cushion or nasal pillows or prongs are not present.

Yet another aspect of the invention relates to a respiratory mask that is wearable by the patient without the cushion.

According to a sample embodiment of the invention, a respiratory mask assembly for delivering a flow of breathable gas to a patient comprises a structure configured to contact a) at least one point on the patient's forehead, b) two points on the patient's temples, the two temple points being on opposite sides of the patient's face, and c) two points on the patient's cheek, the two cheek points being on opposite sides of the patient's face; a frame, being part of the structure, rigidly connected to other elements of the structure and configured to support a cushion in contact with the patient's face; and a plurality of straps connected to the other elements of the structure and configured to hold the structure against the at least one forehead point, the two temple points, and the two cheek points in a fully constrained manner without the presence of a mask cushion or nasal pillows or prongs.

According to another sample embodiment of the invention, a respiratory mask assembly for supporting a patient interface for delivering a flow of breathable gas to a patient comprises a frame configured to support a patient interface in contact with the patient's face; two loop portions extending from opposite sides of the frame, each loop being configured to loop around an ear of the patient; and a strap connecting the two loop portions, the strap being configured to extend laterally across the back of the patient's head.

According to still another sample embodiment of the invention, a respiratory mask assembly for supporting a patient interface for delivering a flow of breathable gas to a patient comprises a main body configured to support a patient interface in contact with the patient's face, the main body being configured to extend from a top of the patient's head to between the patient's eyes; and a support adjustably connected to the main body and configured to engage the back of the patient's head.

Other aspects, features, and advantages of this invention will become apparent from the following detailed description when taken in conjunction with the accompanying drawings, which are a part of this disclosure and which illustrate, by way of example, principles of this invention.

BRIEF DESCRIPTION OF THE DRAWINGS

The accompanying drawings facilitate an understanding of the various embodiments of this invention. In such drawings:

FIGS. 11a and 11b schematically illustrate a patient interface and headgear system according to another sample embodiment of the present invention;

FIGS. 14a-14c schematically illustrate a patient interface and headgear system according to a sample embodiment of the present invention;

DETAILED DESCRIPTION OF ILLUSTRATED EMBODIMENTS

The following description is provided in relation to several embodiments which may share common characteristics and features. It is to be understood that one or more features of any one embodiment may be combinable with one or more features of the other embodiments. In addition, any single feature or combination of features in any of the embodiments may constitute additional embodiments.

In this specification, the word "comprising" is to be understood in its "open" sense, that is, in the sense of "including", and thus not limited to its "closed" sense, that is the sense of "consisting only of". A corresponding meaning is to be attributed to the corresponding words "comprise", "comprised" and "comprises" where they appear.

The term "air" will be taken to include breathable gases, for example air with supplemental oxygen. It is also acknowledged that the blowers described herein may be designed to pump fluids other than air.

The term "mask" refers to nasal masks, full face masks, nasal prongs, cannulae, pillows, nozzles, etc.

Overview of Headgear Forces

Figure 1:
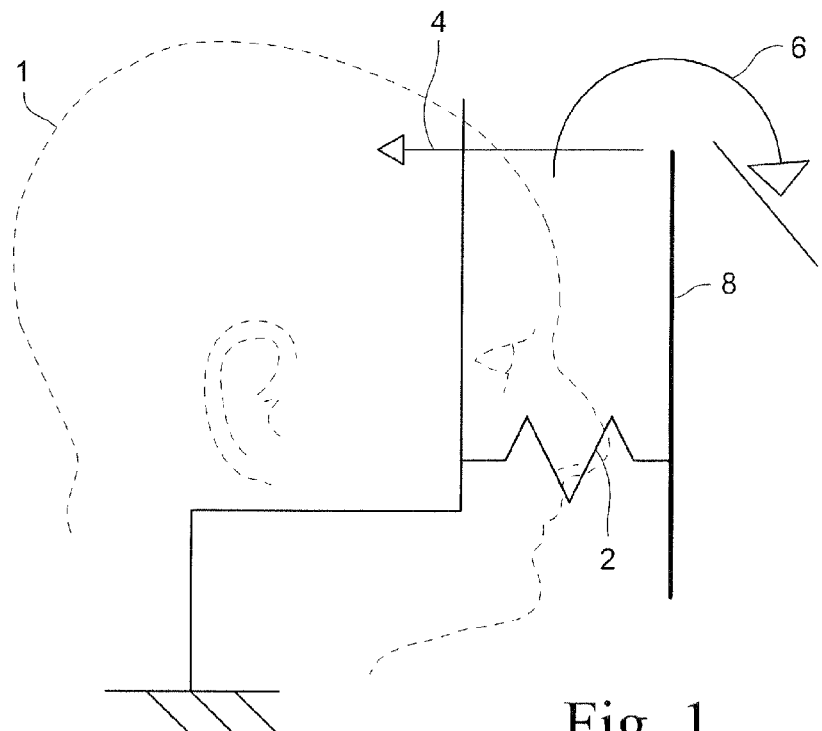
FIG. 1 schematically illustrates the forces as applied by a current headgear and patient interface system.
Figure 2:
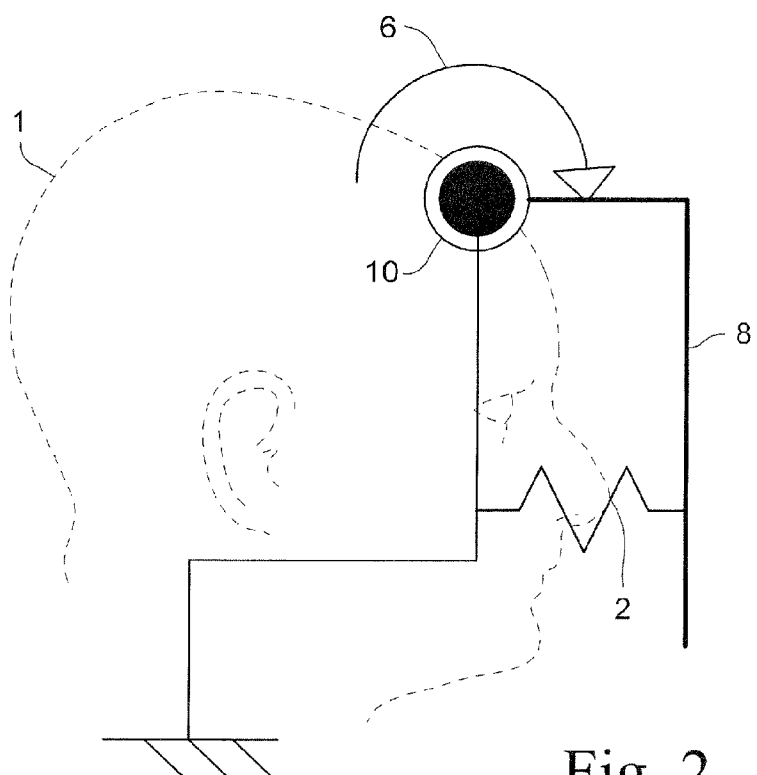
FIG. 2 schematically illustrates the forces applied by another current headgear and patient interface system.
Figure 3A:
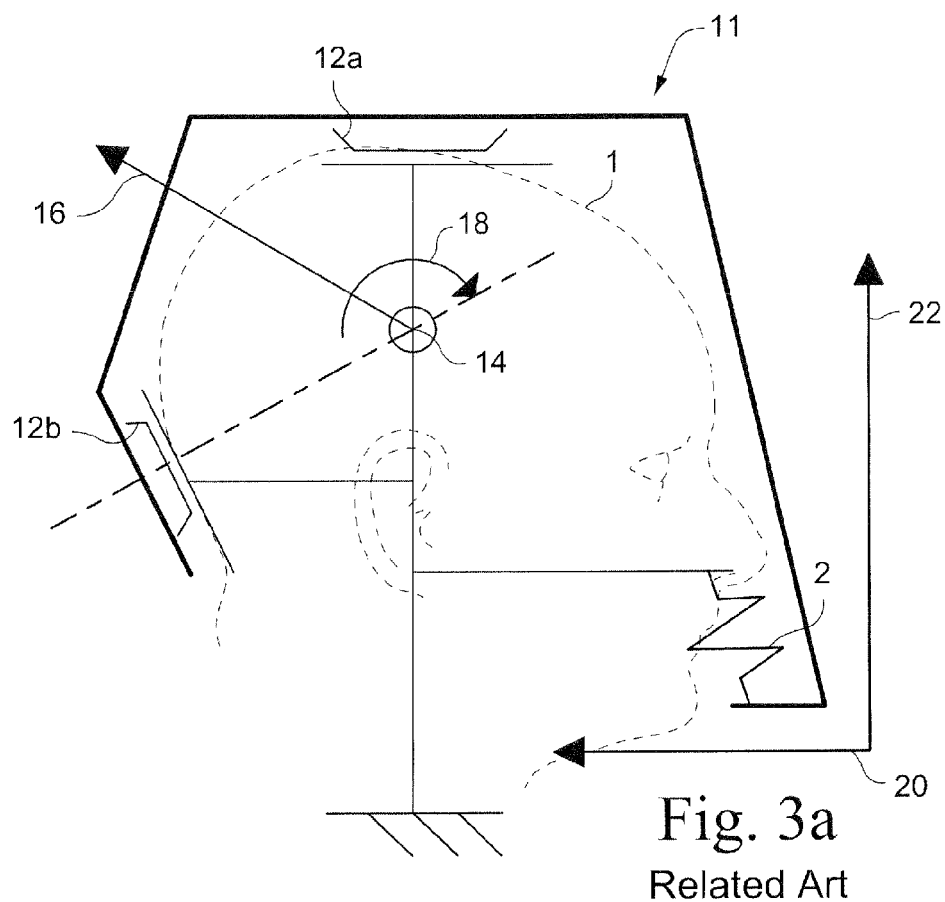
FIGS. 3a-3c schematically illustrate another current headgear and patient interface system and the forces applied thereby.
Figure 3B:
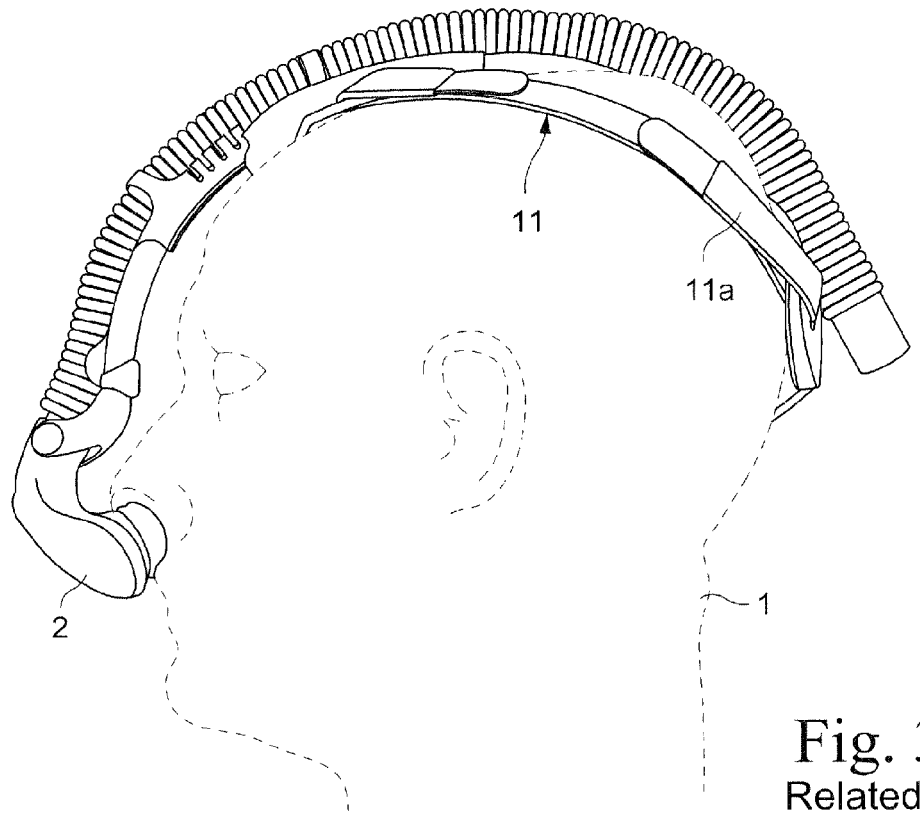
Figure 3C:
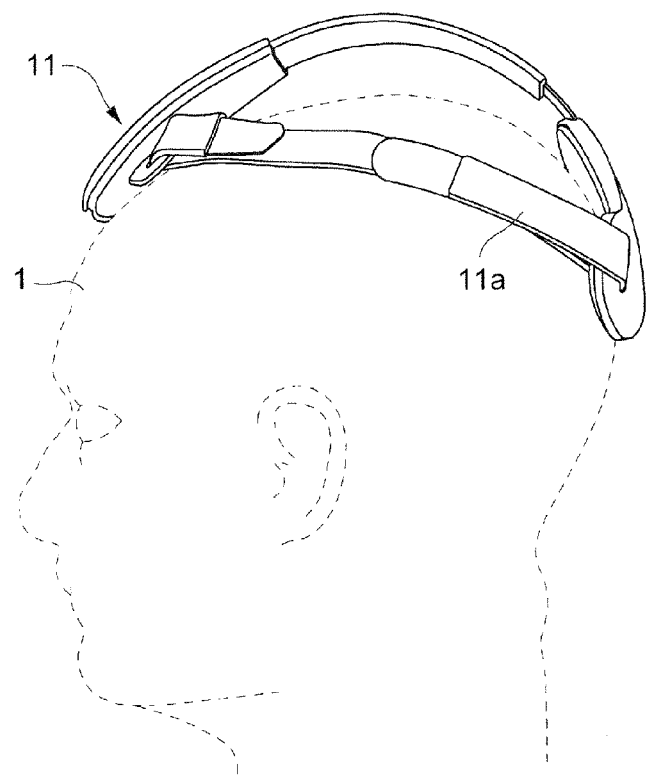
Figure 4A:
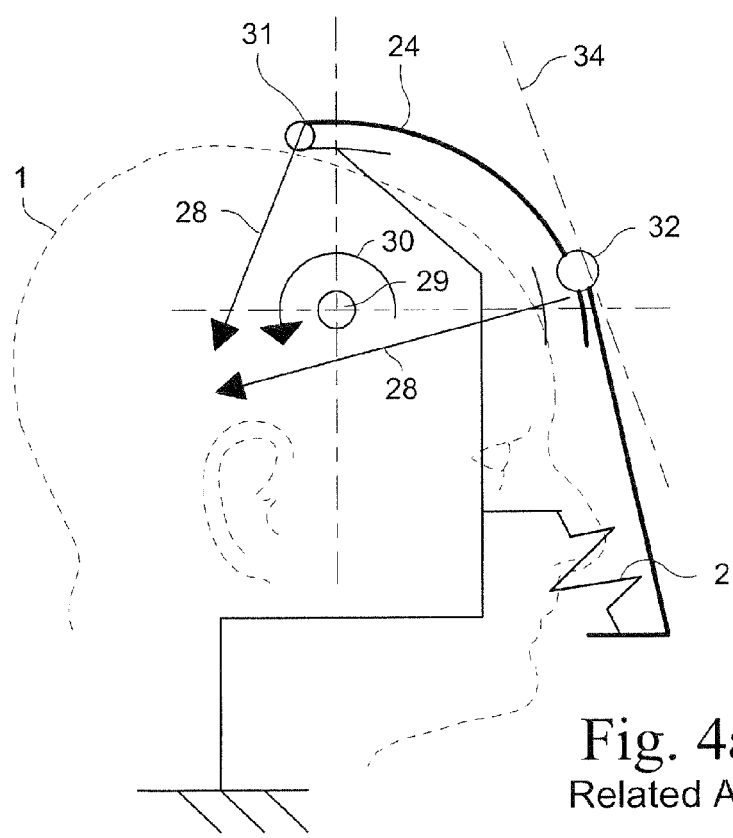
FIGS. 4a-4c schematically illustrate another current headgear and patient interface system and the forces applied thereby.
Figure 4B:
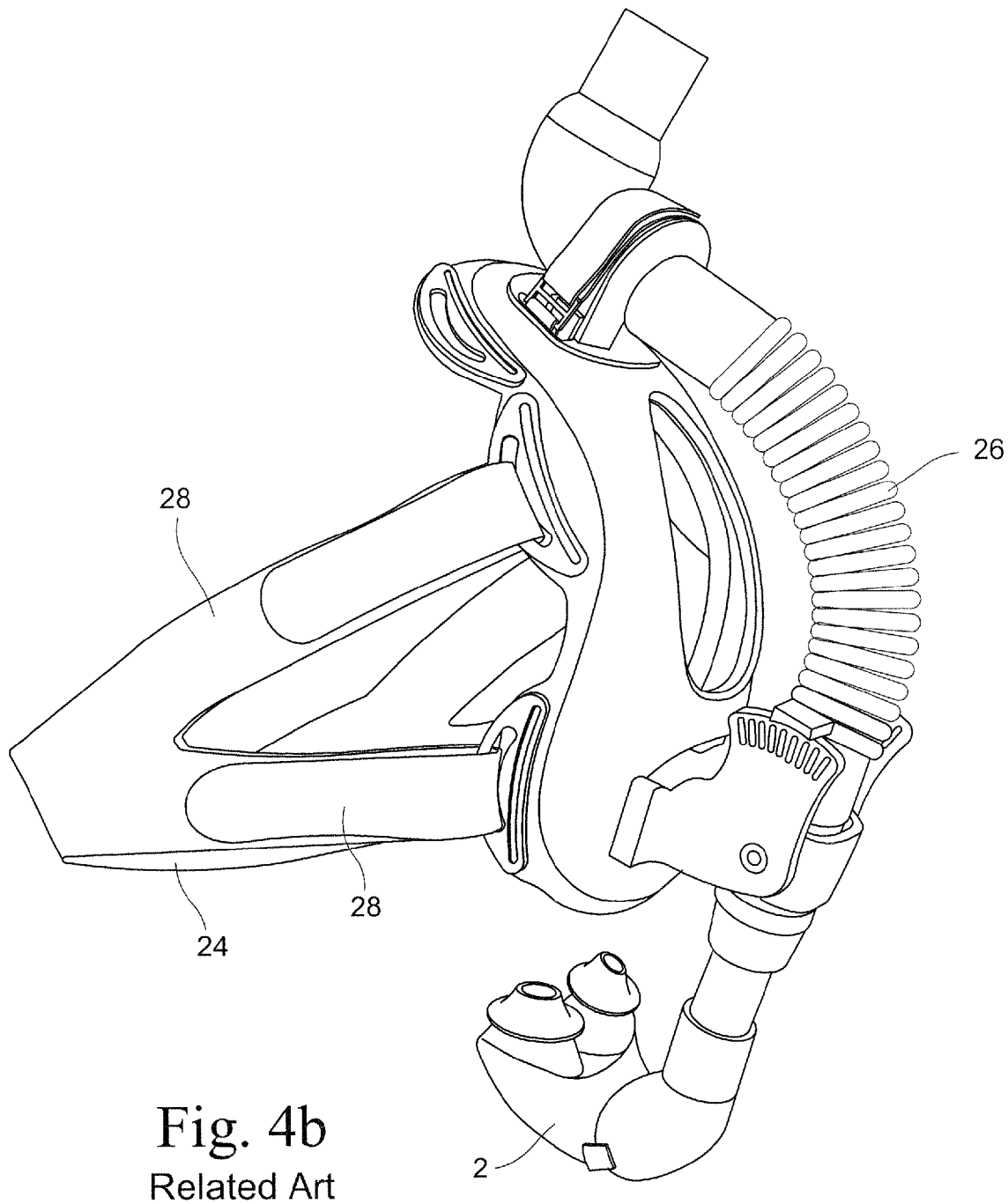
Figure 4C:
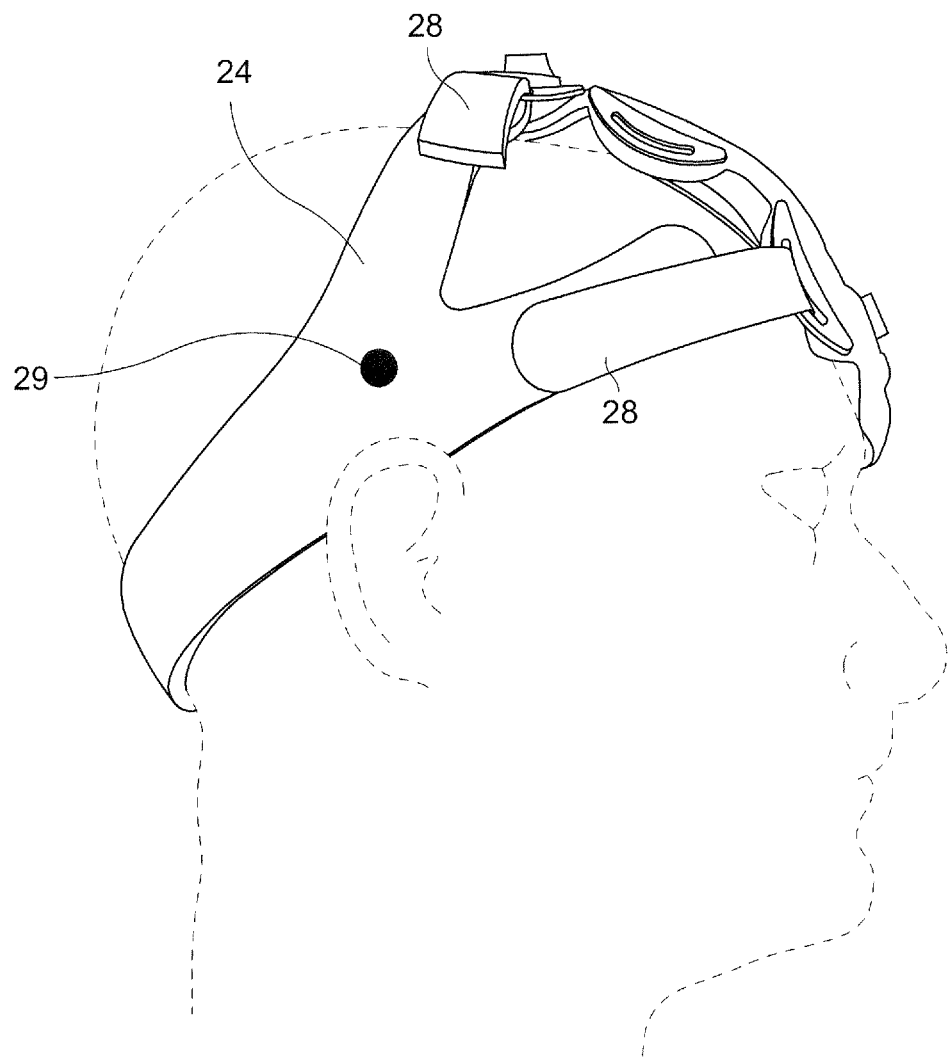
Figure 5A:
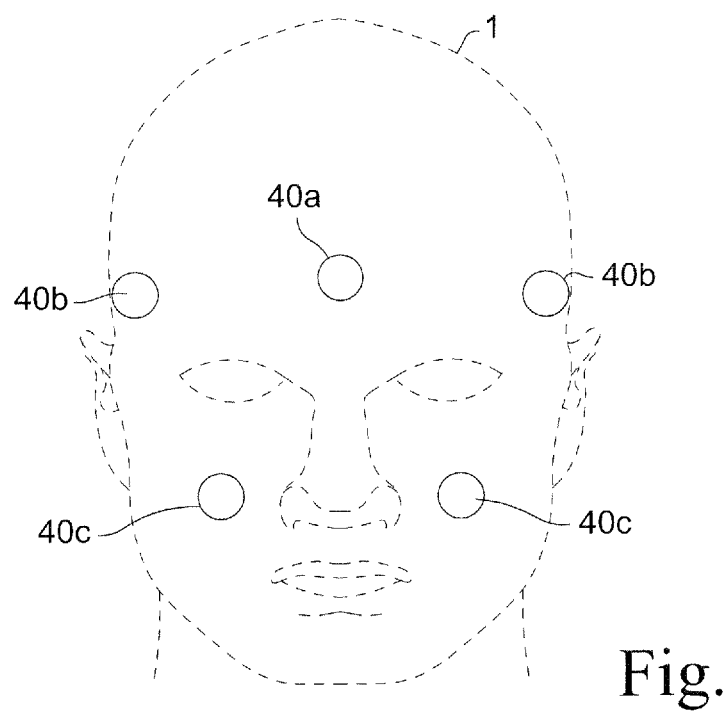
FIGS. 5a-5c schematically illustrate the force as applied by a headgear and patient interface system according to one sample embodiment of the present invention.
Figure 5B:
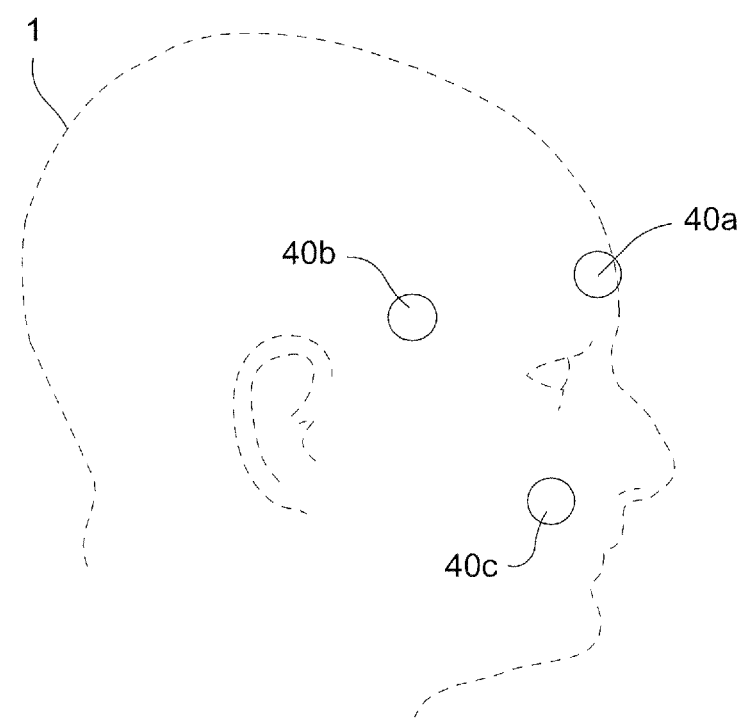
Figure 5C:
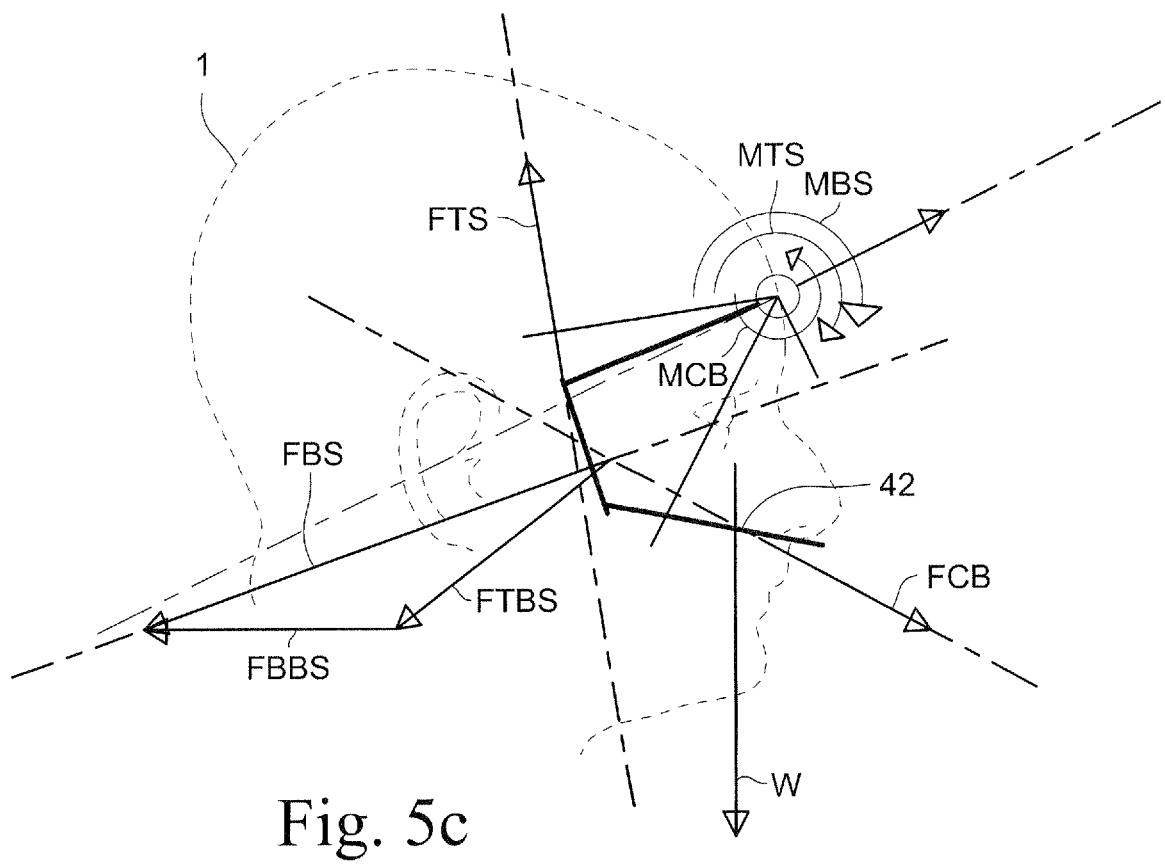

Referring to FIGS. 5a-5c, a patient interface and headgear system according to the present invention includes a main body 42 (FIG. 5c) that is stable on the face of the patient 1 and is configured to compress, or hold in compression, a compliant cushion of the patient interface (not shown) against the face of the patient 1. The main body 42 supports the cushion and the main body 42 can be worn by the patient 1 while the cushion is temporarily removed, for example for cleaning or exchanging with another cushion. The cushion is a deformable component that is provided between the main body 42 and the face of the patient 1 and acting as a seal for the breathable gas required by the therapy. The main body 42 is fully constrained to the head of the patient by the forces applied by straps. The patient interface and headgear system of FIGS. 5a-5c thus does not rely on the stiffness and deformation of the cushion to correctly locate the patient interface against the face of the patient 1.

As shown in FIGS. 5a-5c, the main body 42 is configured to contact the face of the patient 1 at five contact points. The main body 42 contacts the face of the patient 1 at a forehead contact point 40a, temple contact points 40b and cheekbone contact points 40c. The headgear may include a top strap that extends from the temple contact point 40b on the left side of the patient's face to the temple contact point 40b on the right side of the patient's face. The top strap is configured to prevent the main body 42 from falling down off of the head of the patient and may be formed of an elastic material. The top strap need not be configured to support high force values.

The headgear may also include a top back strap and a bottom back strap that extends from the cheekbone contact point 40c on the left side of the patient's face around to the back of the patient's head to the cheekbone contact point 40c on the right side of the patient's face. The back straps are configured to maintain the contact between the patient's face and the main body 42 of the headgear system.

As shown in FIG. 5c, the forces from the straps of the headgear create moments around the forehead contact point 40a. The two reaction forces near the temple contact points 40b are normal to the lateral plane and are not shown in FIG. 5c. The reaction force FCB created at the cheekbone contact points 40c creates a moment MCB that pushes the patient interface away from the face of the patient. The top strap force FTS creates a moment MTS that counterbalances the cheekbone reaction forces FCB, but the top strap force FTS is generated by the elastic deformation of the top strap. The back strap forces FTBS and FBBS create a resulting force FBS that deforms the top strap. The location of the back strap forces is configured to create a stabilizing moment MBS that counterbalances the cheekbone reaction forces. As shown in FIG. 5d, the back strap forces FBBS and FTBS (and resulting force FBS) are applied across the ears of the patient. Accordingly, the headgear system of the present invention may be designed to allow for the application of the appropriate back strap forces without causing discomfort to the patient's ears.

The reaction forces generated at the temple contact points 40b and the cheekbone contact points 40c are normal to the lateral plane and provide lateral stability to the patient interface and headgear system of the present invention. This lateral stability is not provided by the current patient interfaces and headgear systems discussed in the background section of the instant application.

First Embodiment

Figure 6A:
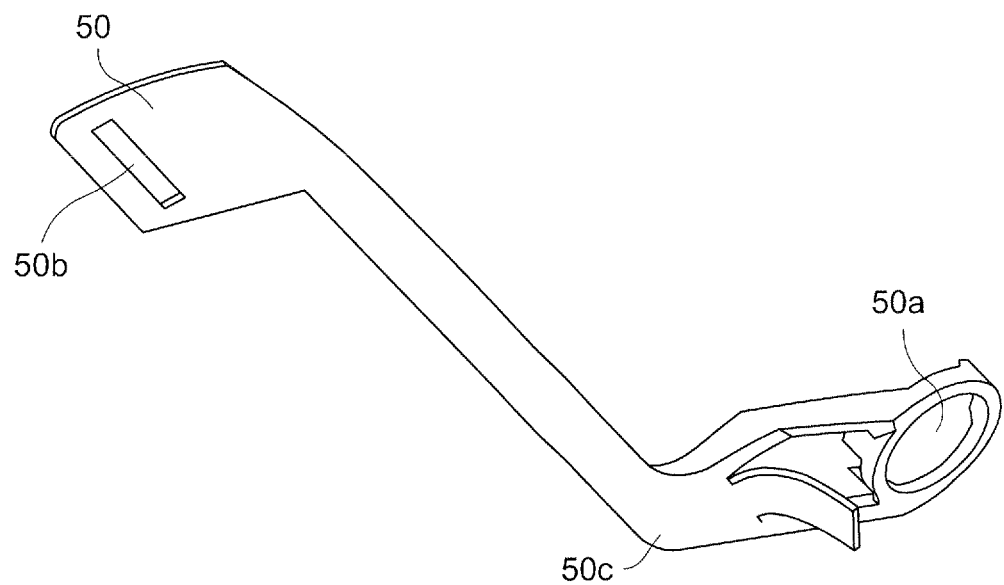
FIGS. 6a and 6b schematically illustrate a sample embodiment of a patient interface and headgear system according to the present invention.
Figure 6B:
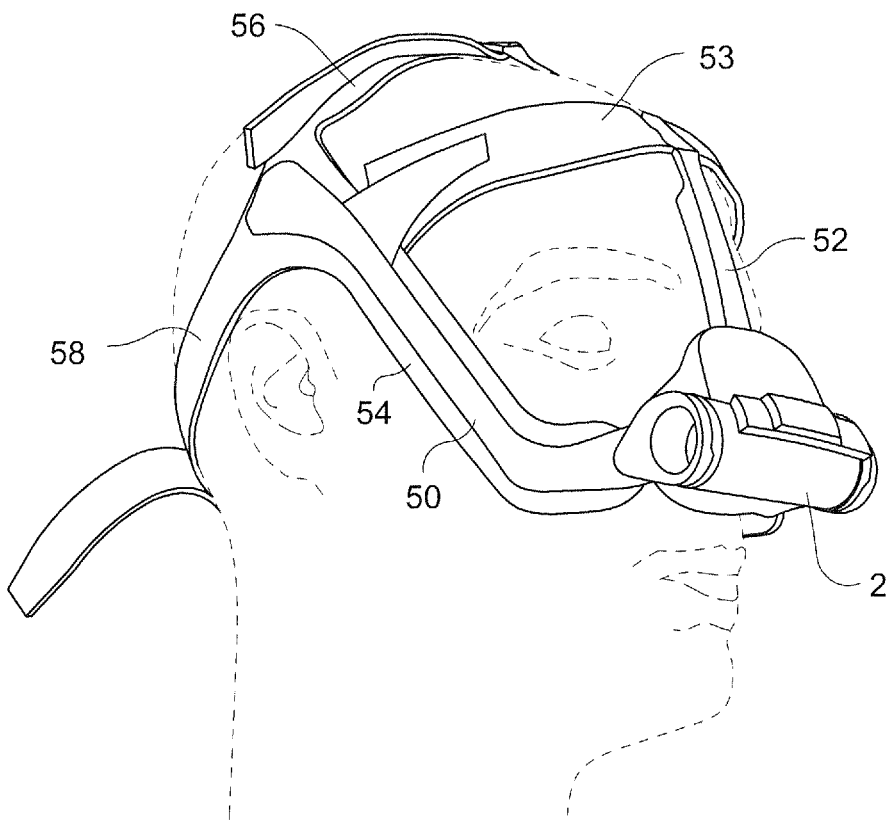

Referring to FIGS. 6a and 6b, a patient interface and headgear system according to a sample embodiment of the present invention includes a pair of yokes 50 (left side shown in FIG. 6a) that connects straps 54, 56 and 58 to a patient interface 2. The patient interface 2 may be a nasal mask including a deformable cushion. The yoke 50 includes a temple portion 50b and a patient interface supporting portion 50a that is configured to support one side of the patient interface 2. Although not shown in the figures, it should be appreciated that a second yoke 50 is provided on the other side of the patient's face shown in FIG. 6b.

The yoke 50 includes a cheekbone portion 50c that is configured to contact the patient's cheekbones. The cheekbone portion 50c helps to stabilize the headgear and the patient interface 2 in contact with the face of the patient. As shown in FIG. 6b, the headgear includes a strap 56 across the top of the patient's head, a stiffening element, or rigidiser, 53 rigidly connected to the yokes 50, across the forehead of the patient, and a strap 58 that extends around a back of the patient's head. A forehead support 52 may also be provided to connect the rigidiser 53 to the patient interface 2 to provide further stabilization of the cushion of the patient interface 2. The rigidiser 53 may be formed as a rigid element to provide a rigid connection between the two yokes 50 of the headgear to provide a precise placement of the frame over the patient's face. The use of the forehead support 52 also avoids the use of forehead pads that support the patient interface, but may block the patient's vision.

The rigidiser 53 may have a fixed length or the length may be adjustable allowing the mask assembly to fit precisely the patient's forehead dimension(s) and profile. The forehead support 52 may provide length adjustability that, together with the possibility of the patient interface 2 to rotate in respect the main body, can allow improved sealing performances on a wide range of facial profiles.

Second Embodiment

Figure 7A:
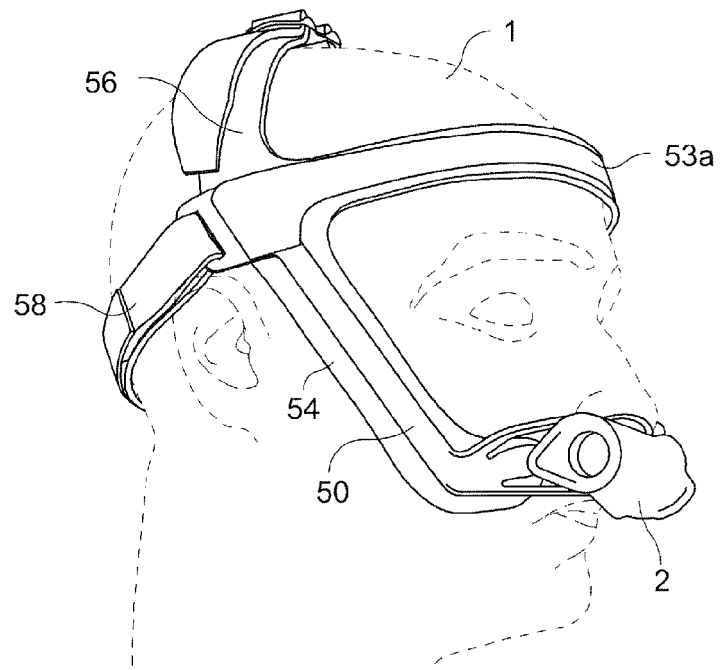
FIGS. 7a and 7b schematically illustrate another sample embodiment of a patient interface and headgear system according to the present invention.
Figure 7B:
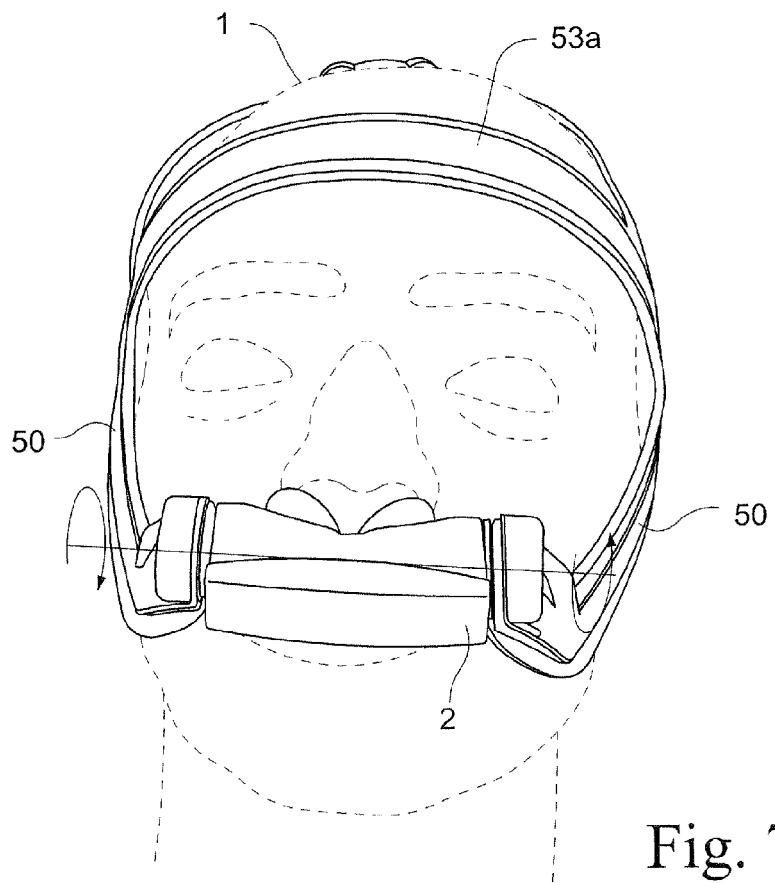

FIGS. 7a and 7b illustrate another sample embodiment of the patient interface and headgear system of the present invention. As shown in FIGS. 7a and 7b, the patient interface 2 is supported by the yokes 50 to be in contact with the face of the patient 1. The headgear includes a top strap 56 that extends across the top of the patient's head and a back strap 58 that extends around the back of the head of the patient. The yokes 50 are connected by a stiffening element, or rigidiser, 53a which extends across the forehead of the patient 1. The rigidiser 53a may be attached to the yokes 50 by, for example, gluing the yokes 50 to the rigidiser 53a. Alternatively, the yokes and rigidiser can be integrally formed, or they can be attached using mechanical structures or hook and loop fasteners, etc. The attachment of the yokes 50 to the rigidiser 53a and the attachment of the patient interface 2 to the yokes 50 forms a rigid closed loop that ensures that the cushion of the patient interface 2 will not rotate and will not lose sealing contact with the face of the patient 1.

Third Embodiment

Figure 8A:
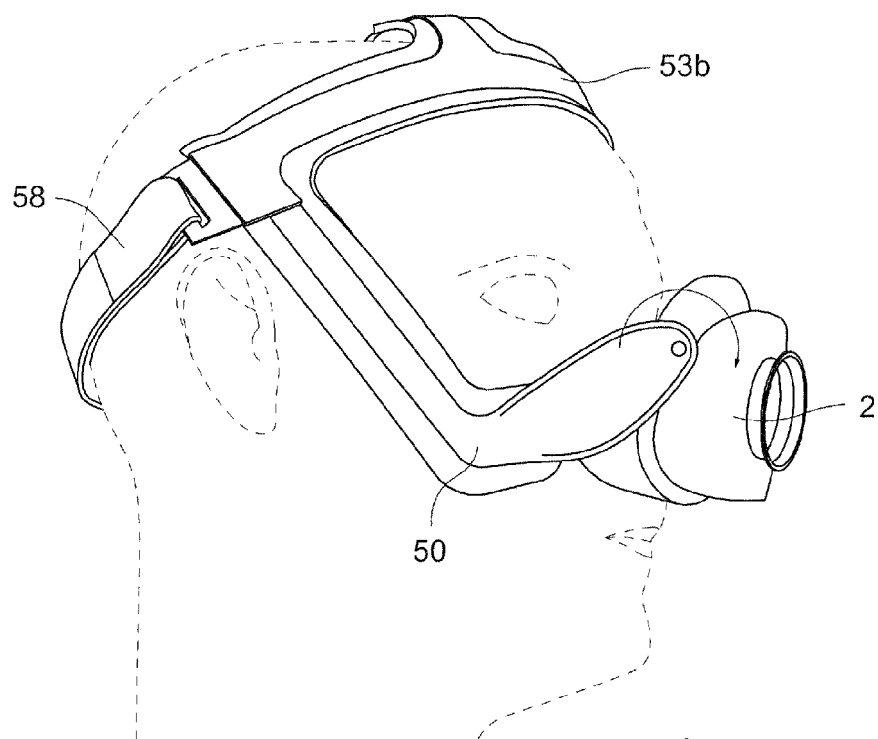
FIGS. 8a and 8b schematically illustrate a patient interface and headgear system according to another sample embodiment of the present invention.
Figure 8B:
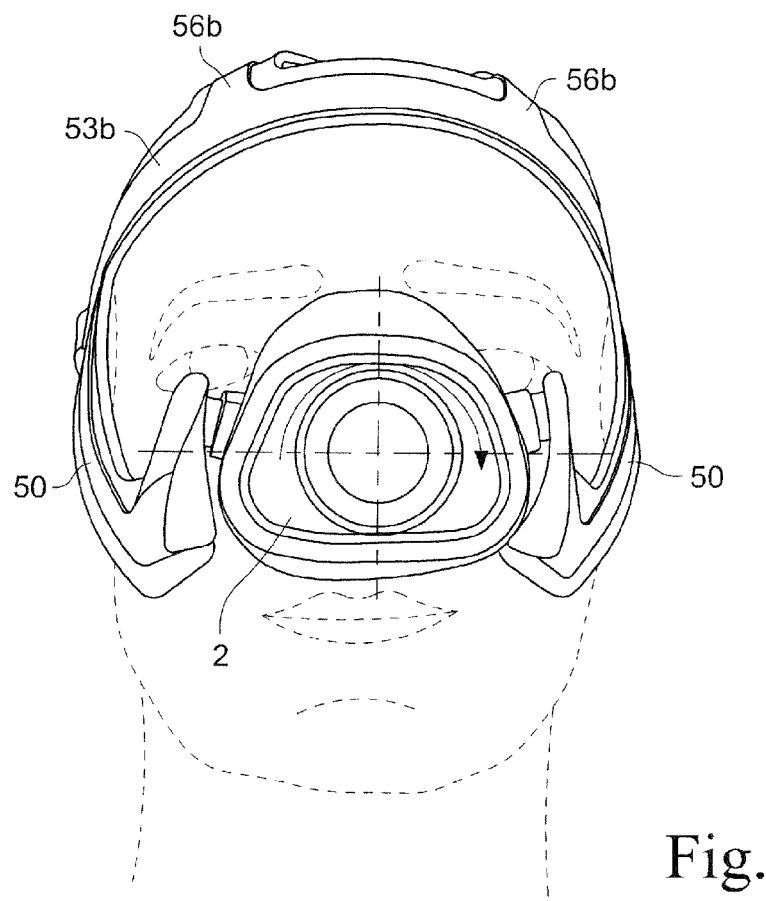

Another sample embodiment of the headgear and patient interface system of the present invention as shown in FIGS. 8a and 8b. The yokes 50 are connected to a rigidiser 53b that includes frame elements 56b that extend over the forehead of the patient 1. The rigid connection of the yokes 50 to the rigidiser 53b and to the patient interface 2 prevent the cushion of the patient interface 2 from rotating around the nose and from losing a proper sealing. The frame elements 56b that extend over the forehead of the patient prevent the patient interface 2 from slipping down the head of the patient 1 and create a moment to push the cushion 2 of the patient interface against the face of the patient.

The cushion of the patient interface 2 may include a gusset to allow proper sealing of any facial profile. The gusset 2 allows the cushion to have relative rotational movement with respect to the yokes 50 and the frame 54 without using a ratchet mechanism on both yokes. The relative rotational movement of the cushion with respect to the yokes 50 and the rigidiser 53b allows for adjustment of the proper sealing fit of the patient interface 2 on the face of the patient 1 and a dual wall cushion is free to comply with the patient's facial profile. Providing a gusset allows this compliance without requiring any intervention from the patient.

Fourth Embodiment

Figure 9:
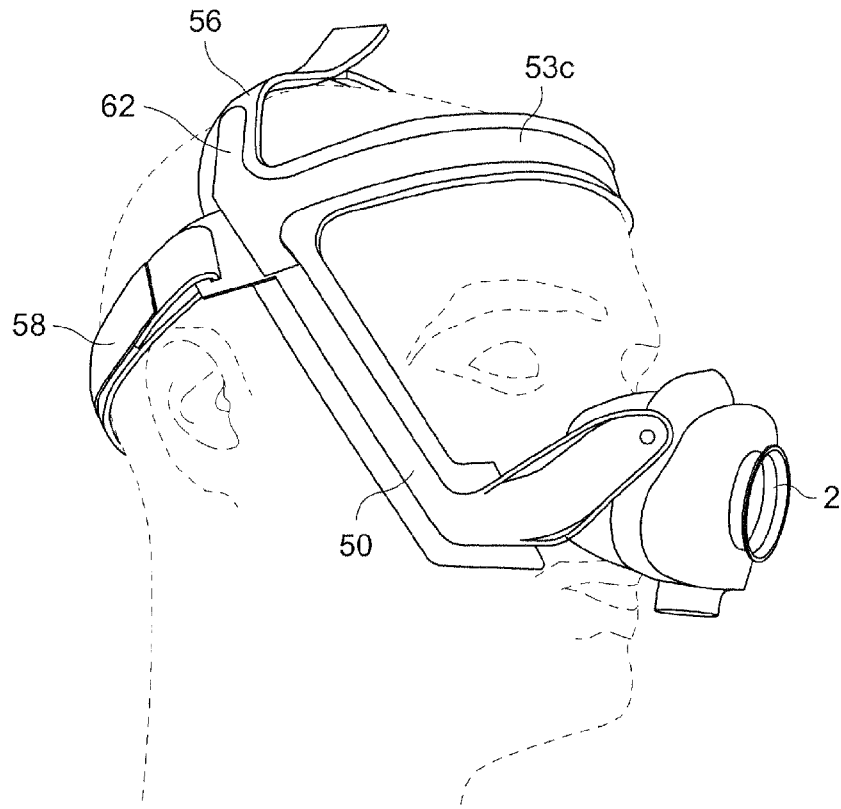
FIG. 9 schematically illustrates a patient interface and headgear system according to another sample embodiment of the present invention.

Referring to FIG. 9, a patient interface and headgear system according another sample embodiment of the present invention includes yokes 50 that are connected to a patient interface 2 that is configured to be in sealing contact with the face of the patient. The rigidiser 53c includes extended portions 62 that support the top strap 56 so that the rigidiser 53c sits in a more natural position on the forehead of the patient. The cushion of the patient interface 2 may be glued to a mask frame or shell and may be formed of a single silicone component incorporating a dual wall cushion, cushion shell and gusset, cushion to frame connection and tube connection. The back strap 58 of the headgear is adjustable so that the force applied by the back strap 58 creates a moment that pushes the rigidiser 53c against the face of the patient. The top strap 56 may be elastic to allow the top strap 56 to conform to different head sizes without adjustment from the patient or the need for multiple size straps.

Fifth Embodiment

Figure 10A:
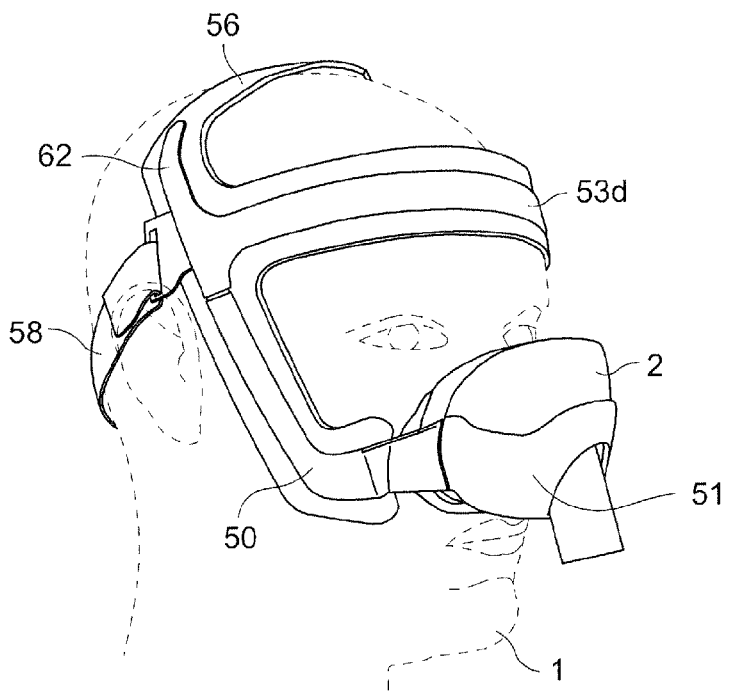
FIGS. 10a-10c schematically illustrate a patient interface and headgear system according to another sample embodiment of the present invention.
Figure 10C:
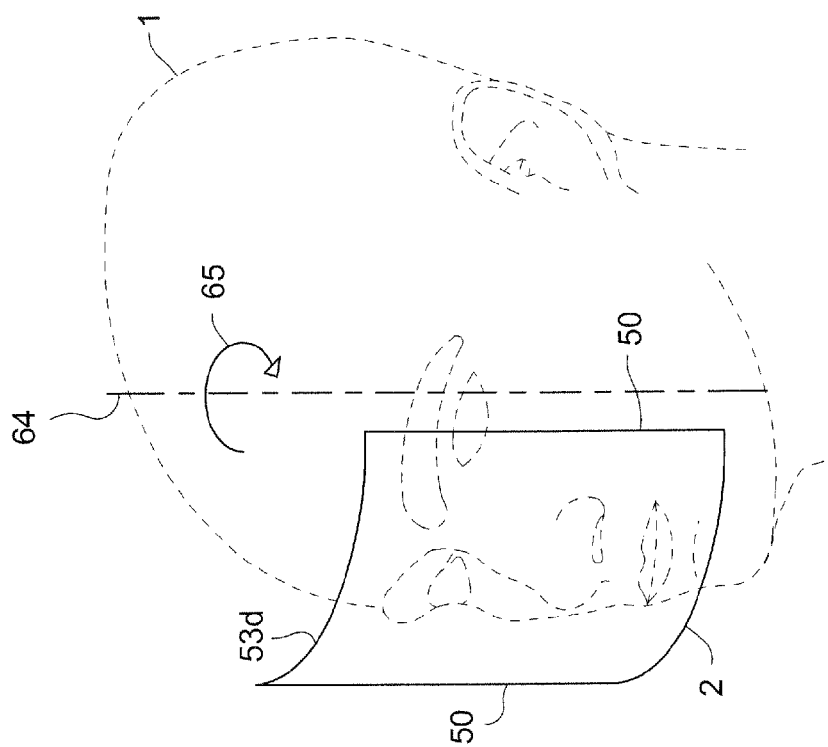
Figure 10B:
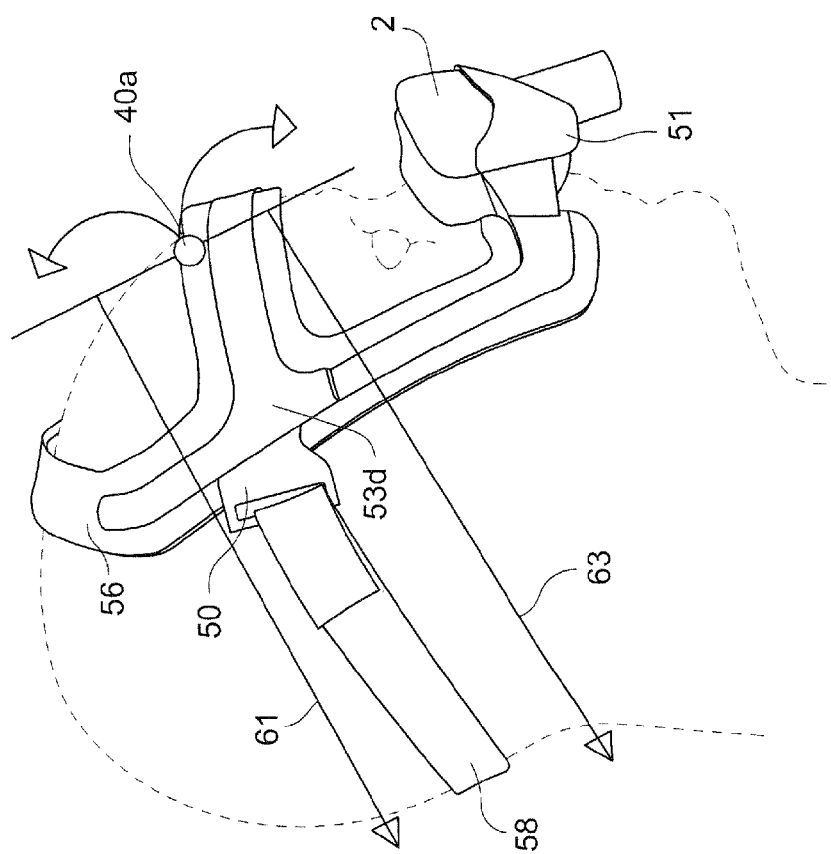

Referring to FIGS. 10a-10c, yokes 50 may be configured to include a supporting portion 51 through which the patient interface 2 may be inserted or otherwise attached. As shown in FIGS. 10b and 10c, the back strap 58 is connected to the yokes 50 so that the back strap does not pull the cushion of the patient interface 2 away from the face of the patient 1. The correct connection is shown by the line 63 (FIG. 10b), which represents the force applied by the back strap 58, while the vector 61 shows how the strap should not be configured because it would pull the patient interface 2 away from the face of the patient. As shown in FIG. 10c, the support for the patient interface 2, the yokes 50, and the rigidiser 53d form a closed structure that can be flexed only by a moment 65 around the axis 64. The main body of the headgear, comprising the yokes 50 and the rigidiser 53d, and the supporting portion 51 may be configured so that they can be manufactured as one single from a heat-formed plastic sheet, or by injection molding.

Sixth Embodiment

The frames of the sample embodiments discussed above may also be implemented into an oro-nasal interface. The top strap 56 and the back strap 58 may be adapted to keep the frame more stable on the face of the patient 1. One problem associated with the use of a single back strap connected above the ears is that such a configuration cannot effectively balance moments generated by an oro-nasal interface. As shown in FIGS. 11*a* and 11*b*, the force 56*a* applied by the top strap 56 and the force 58*a* applied by the back strap 58 create a moment 67 which tends to pull the patient interface 2 away from the face of the patient 1. This imbalance can be corrected by adding a lower strap 57 that applies a force 57*a* to counteract the moment 67. Stabilization of the patient interface mask 2 in sealing contact with the face of the patient can be achieved with a "right-to-left" top strap as previously shown, or may be achieved by a "front-to-back" strap, as shown in FIG. 11*b*. The "front-to-back" strap shown in FIG. 11*b* may employ a Y-shaped top strap 56 to increase the stability of the headgear and to prevent the headgear from slipping down the sides of the head of the patient.

The frame of the headgear and the frame or shell of the patient interface may be formed as one single piece by thermoforming a plastic sheet. The thermoforming process is more efficient than an injection molding process that would require high clamping forces for a mold of such planar dimensions. The frame of the headgear may also be thermoformed separately from the shell or frame of the patient interface that supports the cushion. The thermoforming process in this embodiment is quicker and simpler than other processes which obtain the frame 54 and the shell as one single piece, as injection molding for example. The shell of the patient interface can then be injection molded and the two components can be connected with, for example, a snap-fit. Although this may increase the number of parts, the thermoforming process is less demanding and allows increased flexibility for the patient since the patient will be able to slip on and off the entire mask, or just take off the shell and cushion while still wearing the headgear with the frame.

The yokes 50 and the rigidiser 53-53*d* may be provided with soft padding that may be, for example, glued to the yokes 50 and to the rigidiser 53-53*d*. The soft padding maybe formed of Breathoprene™ that may be cut to match the shape of the yokes 50 and the rigidiser 53-53*d*. This process allows a good level of material efficiency.

Alternatively, the soft padding may be cut in two strips. One strip would incorporate the yoke padding and the top strap and the second strip would incorporate the padding for the frame of the headgear. The two strips could then be glued to the yokes and rigidiser. Although this process may involve handling of an additional component, it greatly reduces the amount of scrap material generated.

It should be appreciated that the frame, the padding and the straps may be formed of various materials using various processes. For example, the padding may be formed by overmolding of thermoplastic elastomer (TPE) or silicone rubber over plastic components.

Seventh Embodiment

Figure 12A:
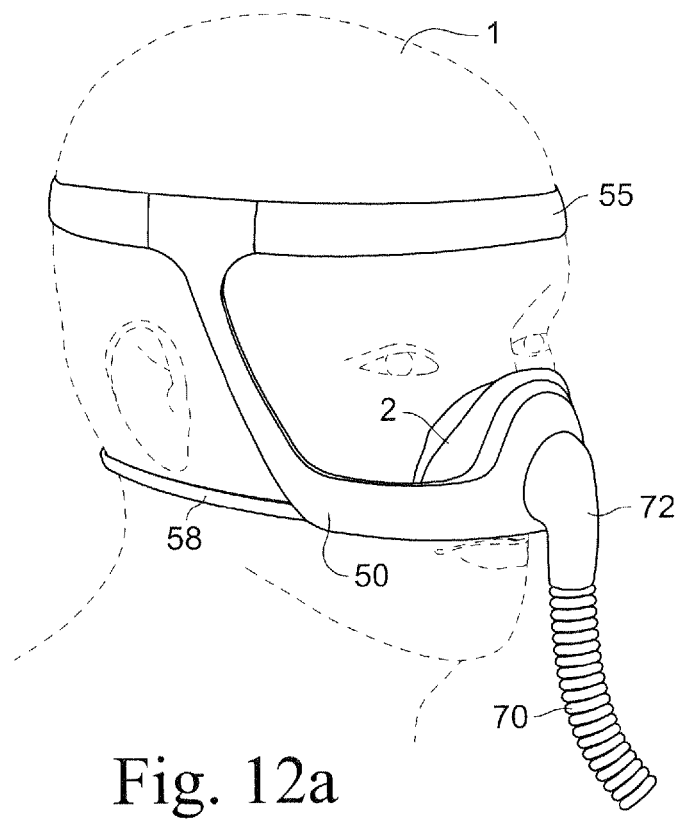
FIGS. 12a-12c schematically illustrate a patient interface and headgear system according to a sample embodiment of the present invention.
Figure 12B:
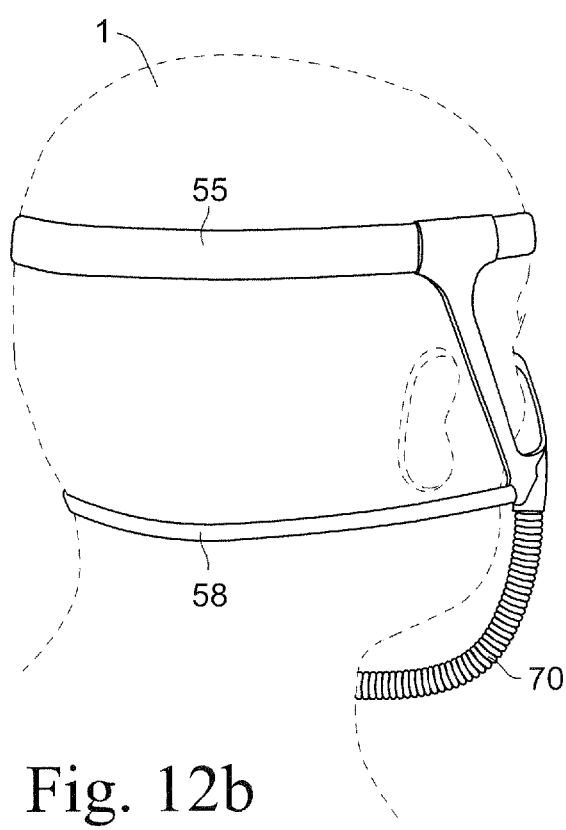
Figure 12C:
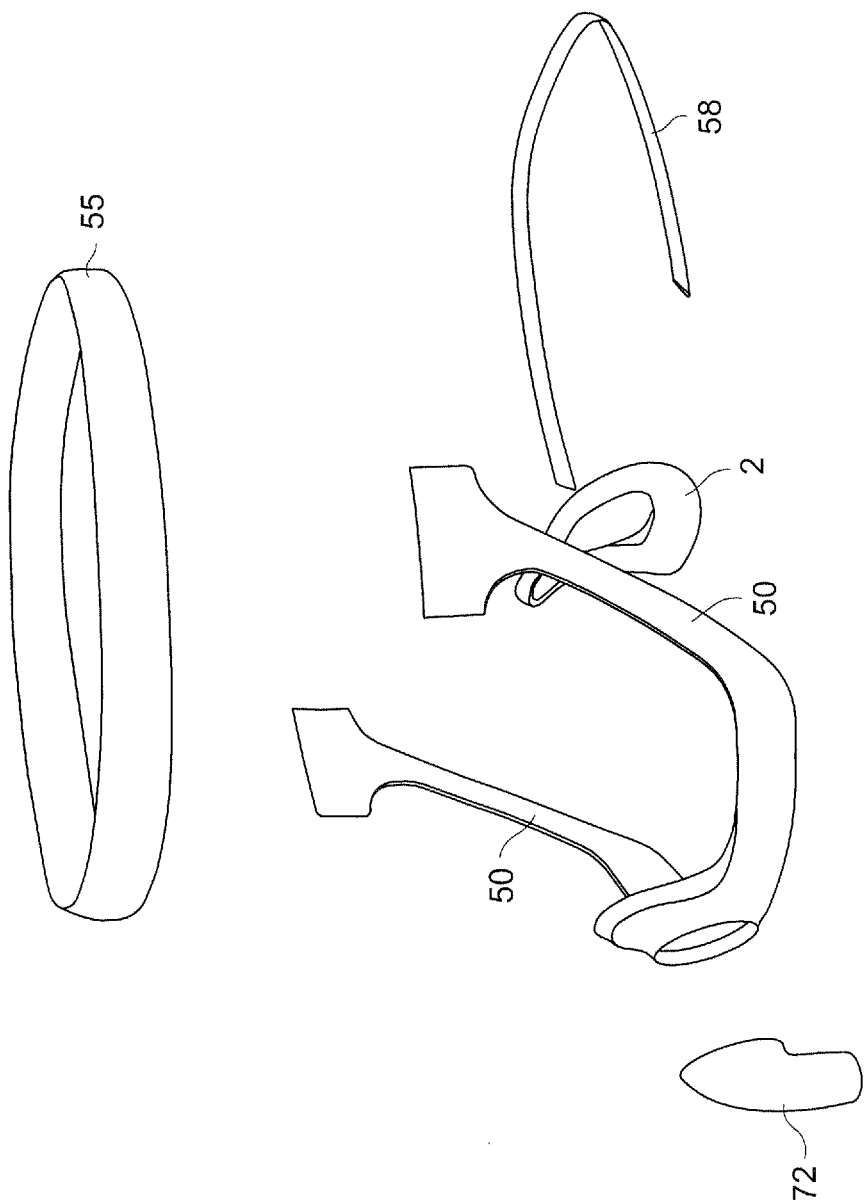

Referring to FIGS. 12*a*-12*c*, a patient interface and headgear system according to a sample embodiment of the present invention includes a frame 55 that may be formed as a headband. The headband may include an adjustment mechanism, for example like a slider with a ratchet. The yokes 50 may be formed as an injection molded main body. The patient interface 2 may be a silicone cushion based mask. For example, the patient interface 2 may be the Swift™ mask manufactured by ResMed Ltd., the assignee of the application. The air delivery hose or conduit 70 may be connected to the mask 2 by a swivel elbow 72 that is connected to the main body formed by the yokes 50, or by a gimbal built with soft rubber and TPE or silicone. The headgear may also include a lower strap 58 that extends around the back of the patient's head.

Eighth Embodiment

Figure 13A:
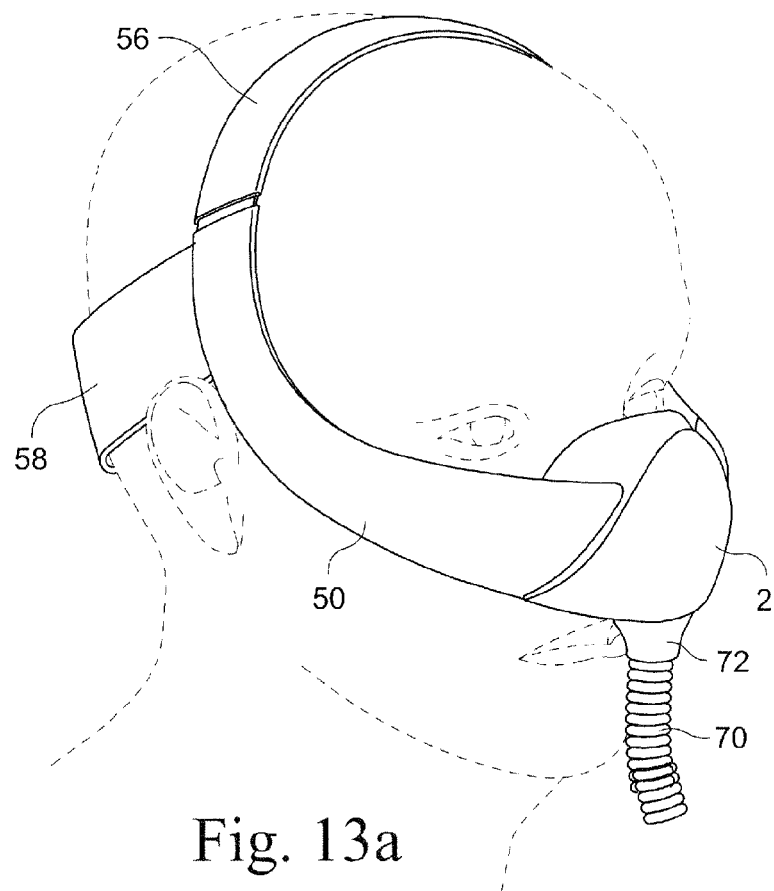
FIGS. 13a-13c schematically illustrate a patient interface and headgear system according to a sample embodiment of the present invention.
Figure 13B:
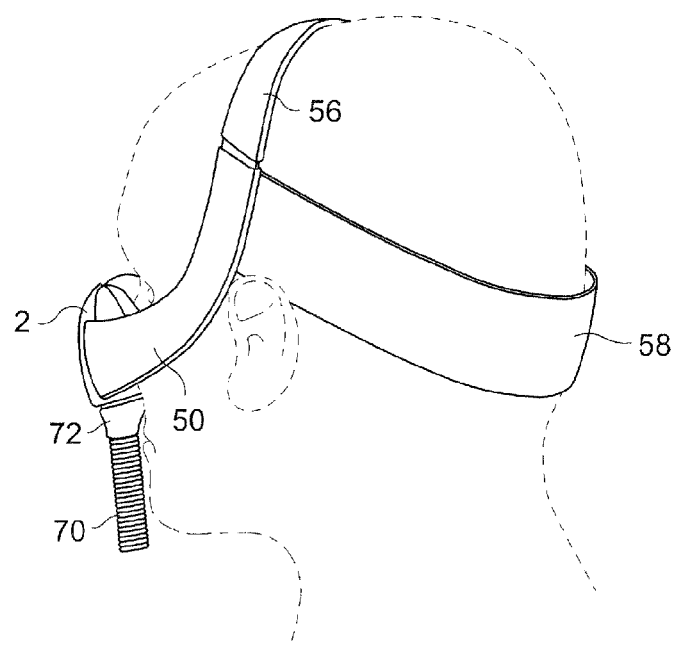
Figure 13C:
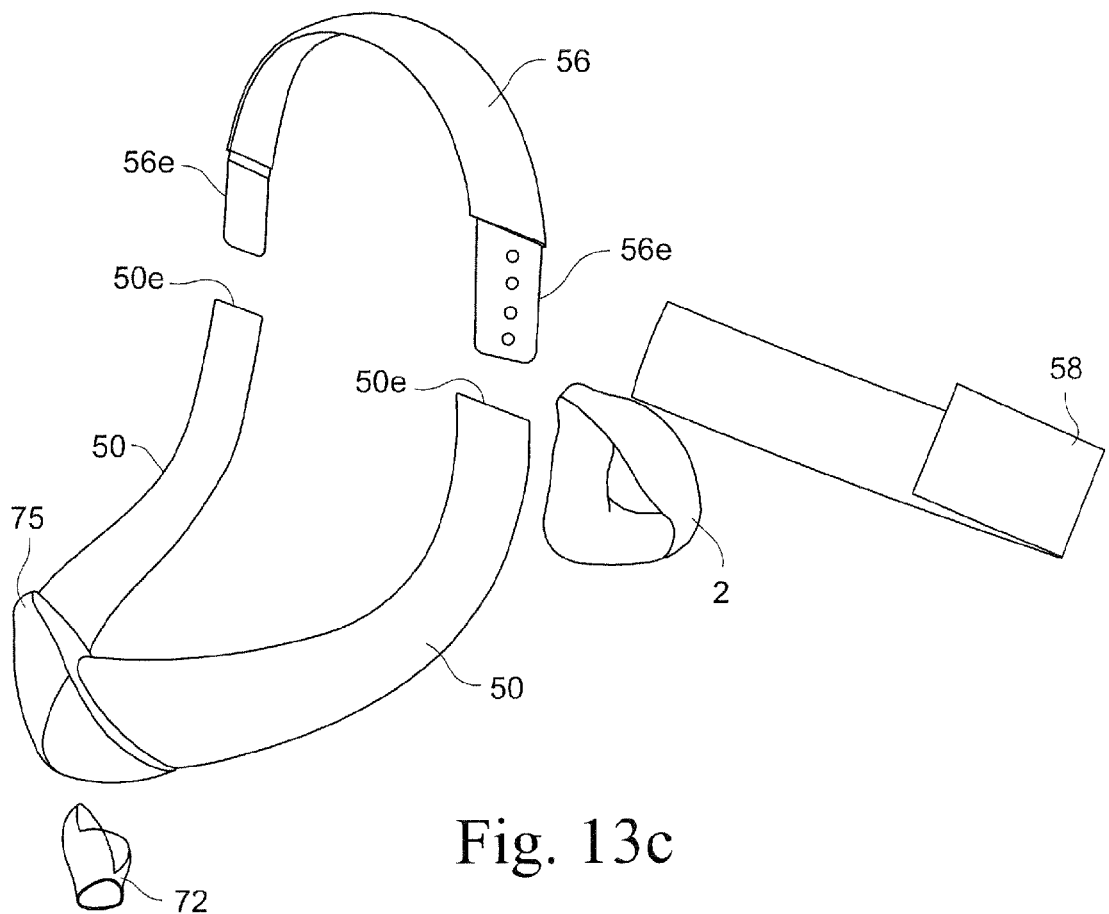

As shown in FIGS. 13*a*-13*c*, a patient interface and headgear system according to another sample embodiment of the present invention includes yokes 50 which are connected to a top strap 56 for contacting the face of the patient. The top strap 56 should be rigid across its width yet flexible along its length and its length should include an adjustment mechanism, like a slider with a ratchet for example. A back strap 58 is provided to keep the patient interface 2 in sealing contact with the face of the patient 1. The patient interface 2, which may be a silicone cushion, is supported by a main body 75 attached to the yokes 50. The patient interface 2 may be connected to the conduit 70 by a hose pivot 72 or by a gimbal made of rubber material like TPE or silicone. The gimbal may be formed in one piece with the cushion. The patient interface 2 may include a silicone cushion, such as the Visa™ or Swift™ manufactured by the assignee ResMed Ltd. The yokes 50 and the top strap 56 may be co-molded polycarbonate and TPU. The ends 56*e* of the top strap 56 may be adjustably insertable into the ends 50*e* of the yokes 50. The back strap 58 may be a breathable woven elastic strap. Cheek supports may be included in the yokes 50. In this embodiment, the forehead contact point is moved back on the frontal part of the patient's head.

Ninth Embodiment

Figure 14A:
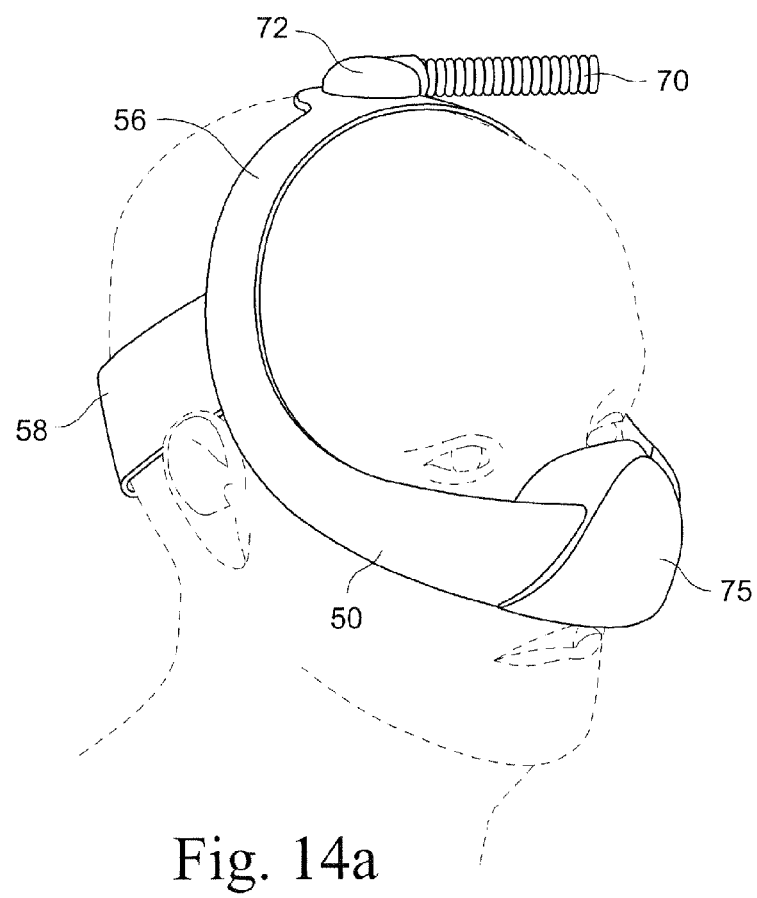
Figure 14B:
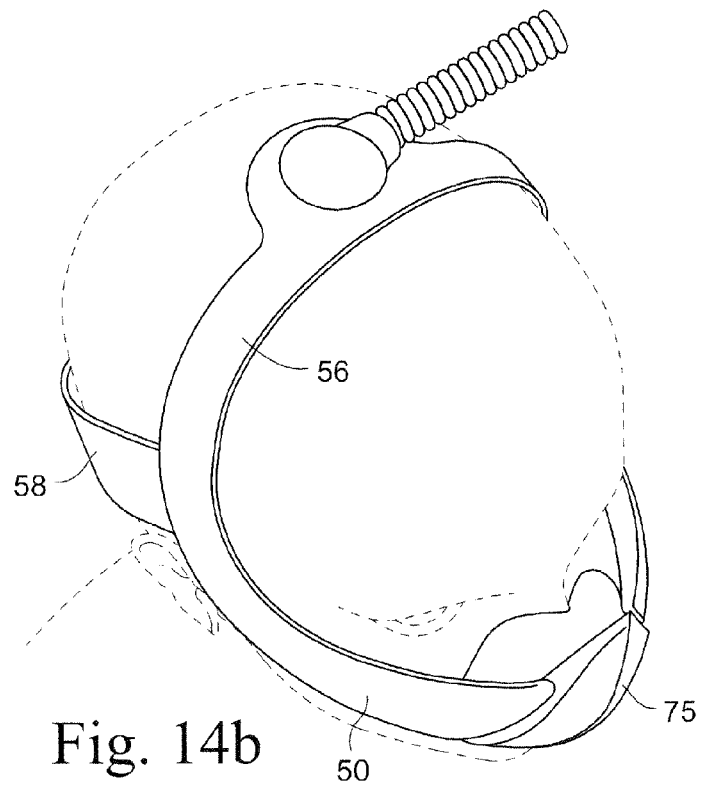

As shown in FIGS. 14*a*-14*c*, the yokes 50 and the top strap 56 of the headgear may be formed as a gas injection molded head strap. The conduit 70 may be connected to the top of the top strap 56 by a hose swivel, or gimbal, 72. A back strap 58, for example, a breathable woven elastic strap, may be connected to the top strap 56 to maintain sealing contact of the patient interface 2 with the face of the patient. The patient interface 2, which may be a silicone cushion, is supported by a main body 75 attached to the yokes 50. The yokes 50 and the top strap 56 may be formed as air delivery conduits, tubes, or hoses and may include adjustment mechanism that can vary in length.

Tenth Embodiment

Figure 15A:
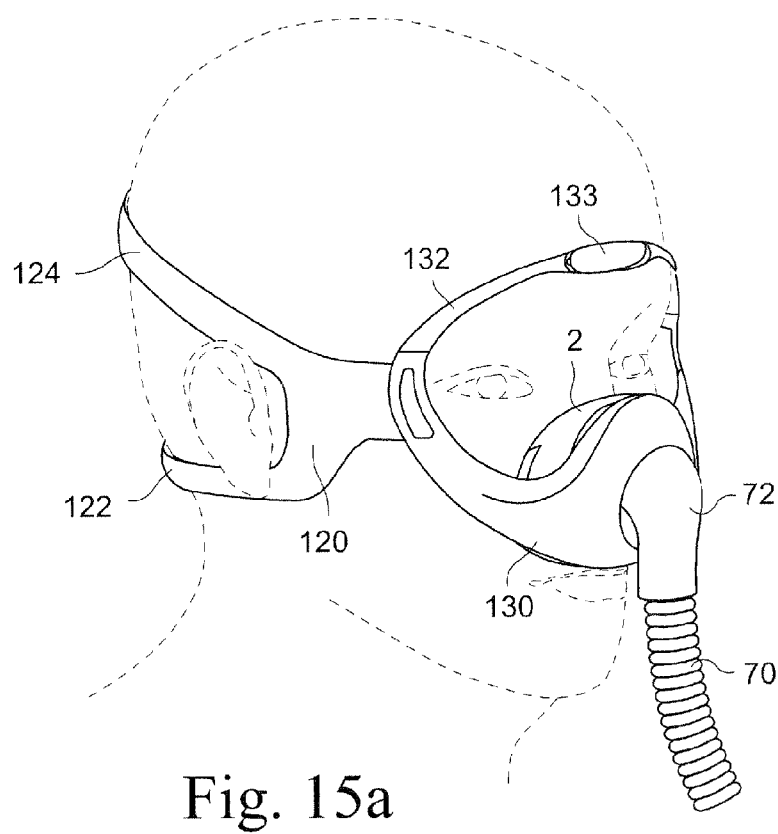
FIGS. 15a-15c schematically illustrate a patient interface and headgear system according to a sample embodiment of the present invention.
Figure 15B:
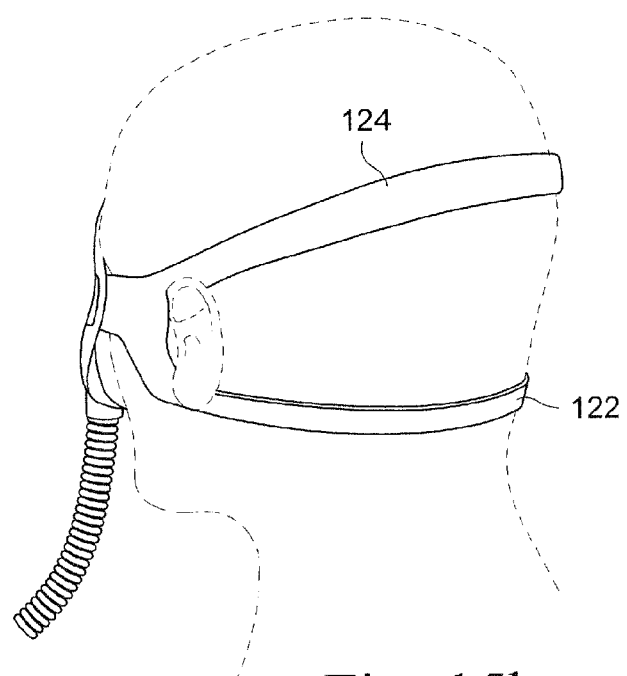
Figure 15C:
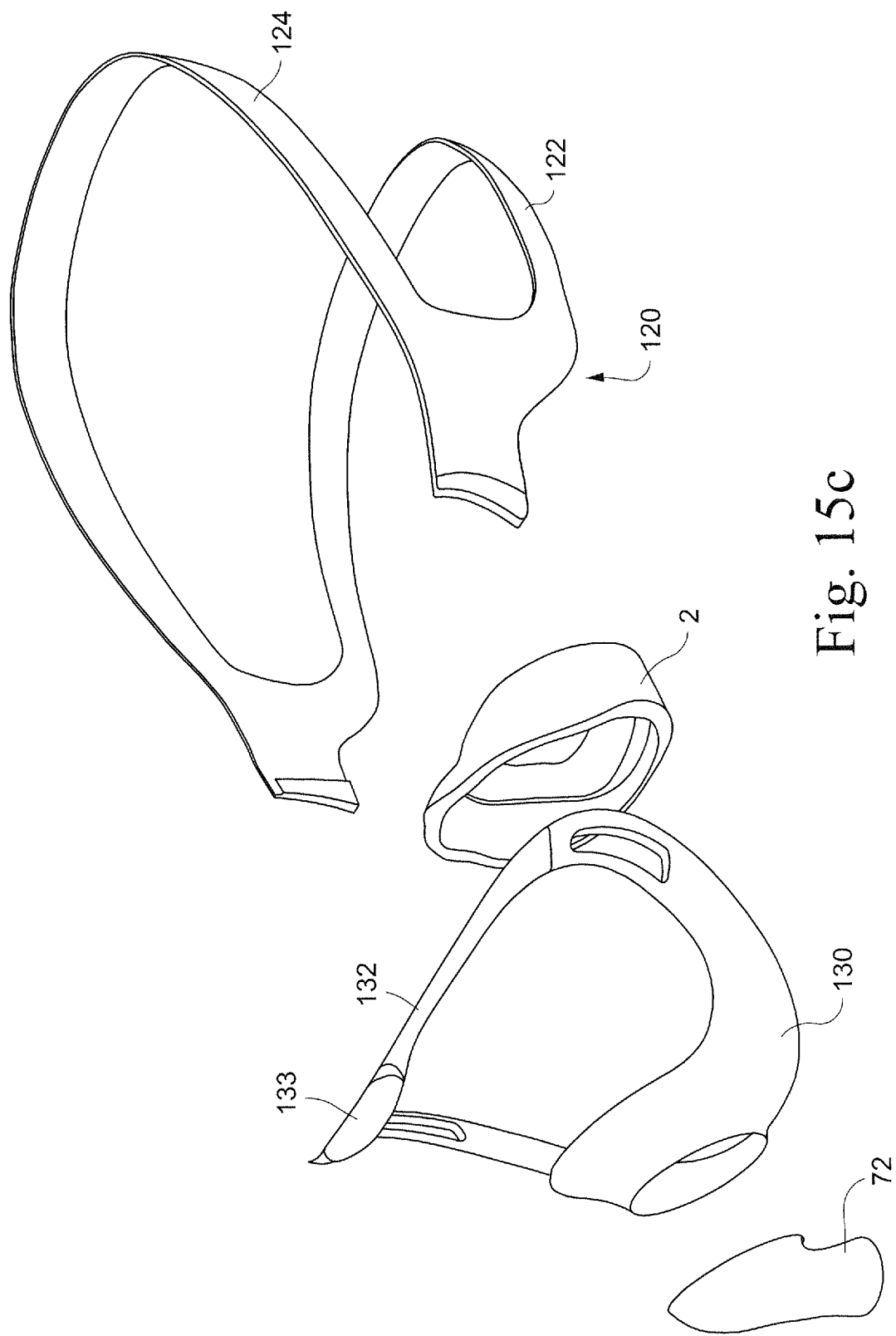

Referring to FIGS. 15*a*-15*c*, a patient interface and headgear system includes a main body 120 having lower and upper straps 122 and 124, respectively, which extend around the back of the patient's head. The headgear main body 120 is connected to a patient interface support 130 that supports the patient interface 2. The patient interface support 130 includes a stabilizing element 132 which extends across the forehead of the patient to stabilize the patient interface 2 in sealing contact with the face of the patient. A flow of breathable gas is delivered by a conduit 70 which is connected to the patient interface support 130 by a hose pivot 72.

Eleventh Embodiment

Figure 16A:
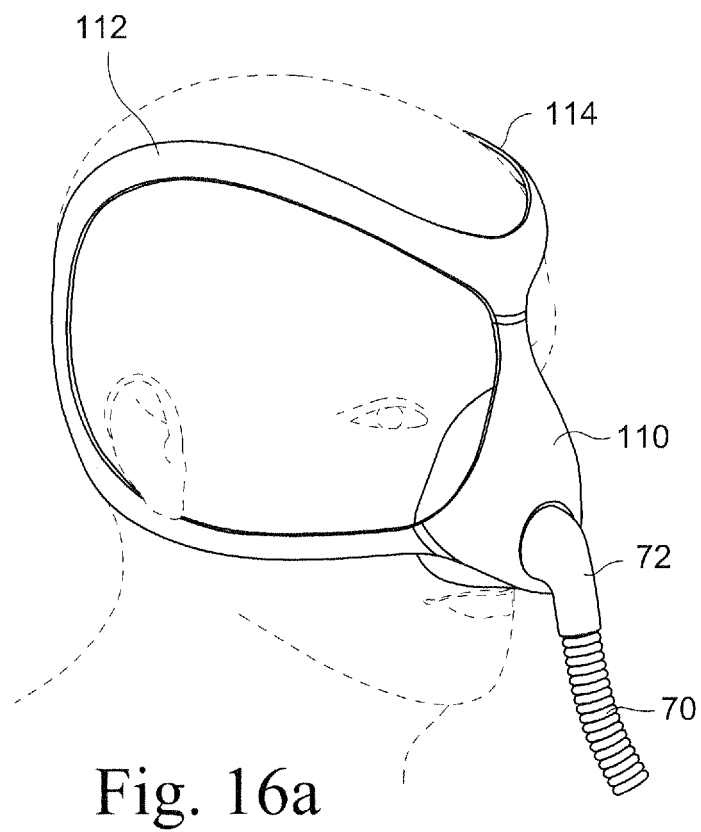
FIGS. 16a-16c schematically illustrate a patient interface and headgear system according to a sample embodiment of the present invention.
Figure 16B:
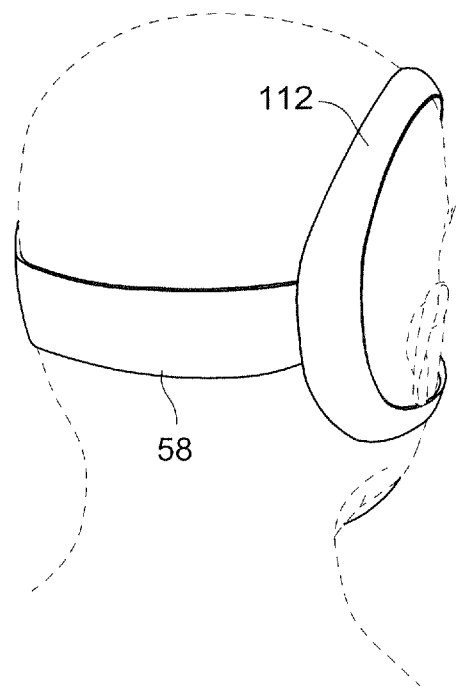
Figure 16C:
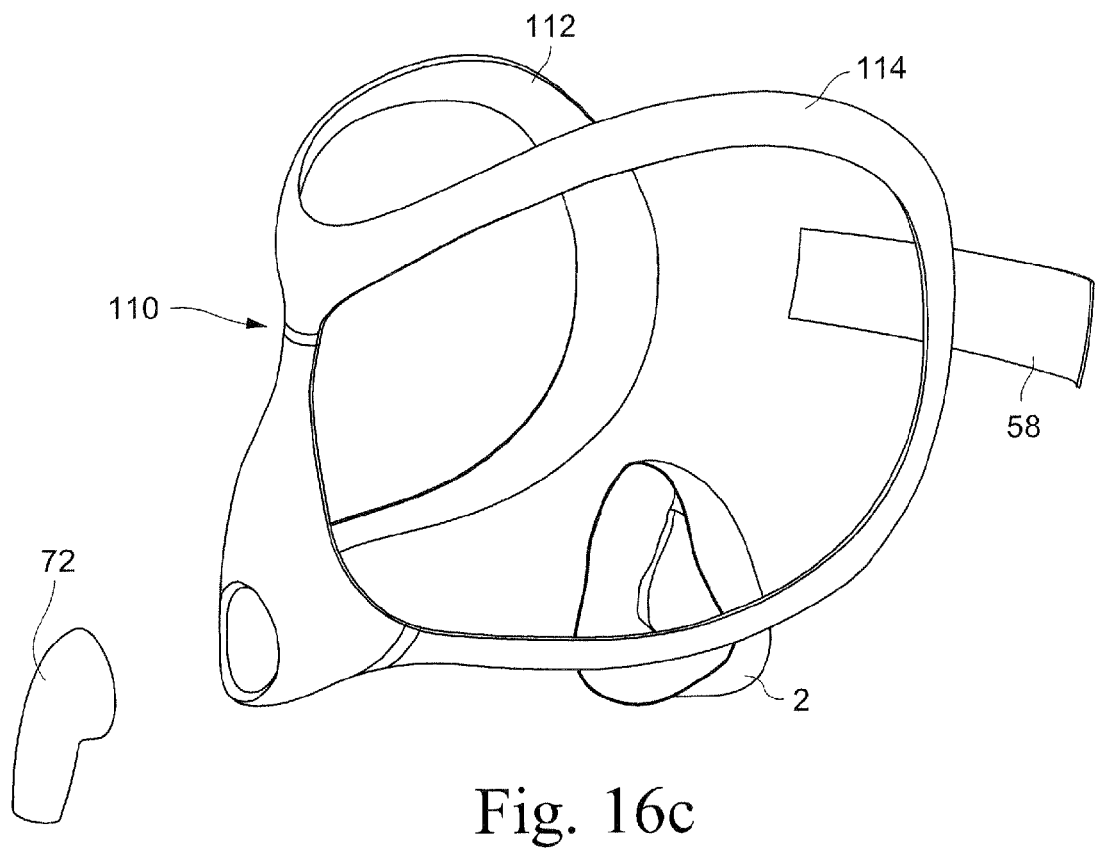

Referring to FIGS. 16*a*-16*c*, a patient interface and headgear system according to another sample embodiment includes a co-molded main body 110 that includes looped portions 112, 114 that loop around the ears of the patient. A back strap 58 may also be provided to maintain the sealing contact of the patient interface 2 with the face of the patient. The back strap 58 may be a woven fabric strap, or may be an adjustable strap. The patient interface 2 may be a silicone or foam cushion. A flow of breathable gas is delivered by a conduit 70 which is connected to the main body 110 by a hose pivot 72.

Twelfth Embodiment

Figure 17:
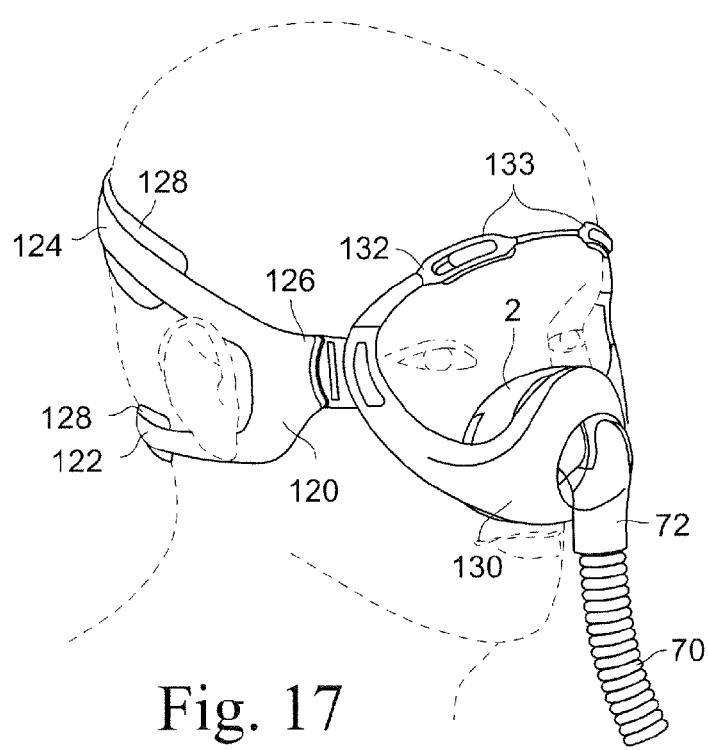
FIG. 17 schematically illustrates a patient interface and headgear system according to a sample embodiment of the present invention.

As shown in FIG. 17, the main body 120 may include an adjustable portion 126 which allows the lower and upper straps 122 and 124 to be adjusted. Additional padding 128 may be provided to the lower and upper straps 122, 124 for rear strap support and comfort. The stabilizing element 132 may include a forehead stabilizing element 133 to engage the forehead of the patient. A flow of breathable gas is delivered by a conduit 70 which is connected to the patient interface support 130 by a hose pivot connection 172.

The stabilizing element 132 of the patient interface support 130 may include an adjustable forehead stabilizing element(s) 133a that allows the length of the stabilizing element 132 to be varied, and allows the position(s) of the forehead stabilizing element(s) 133a to be varied.

Thirteenth Embodiment

Figure 18:
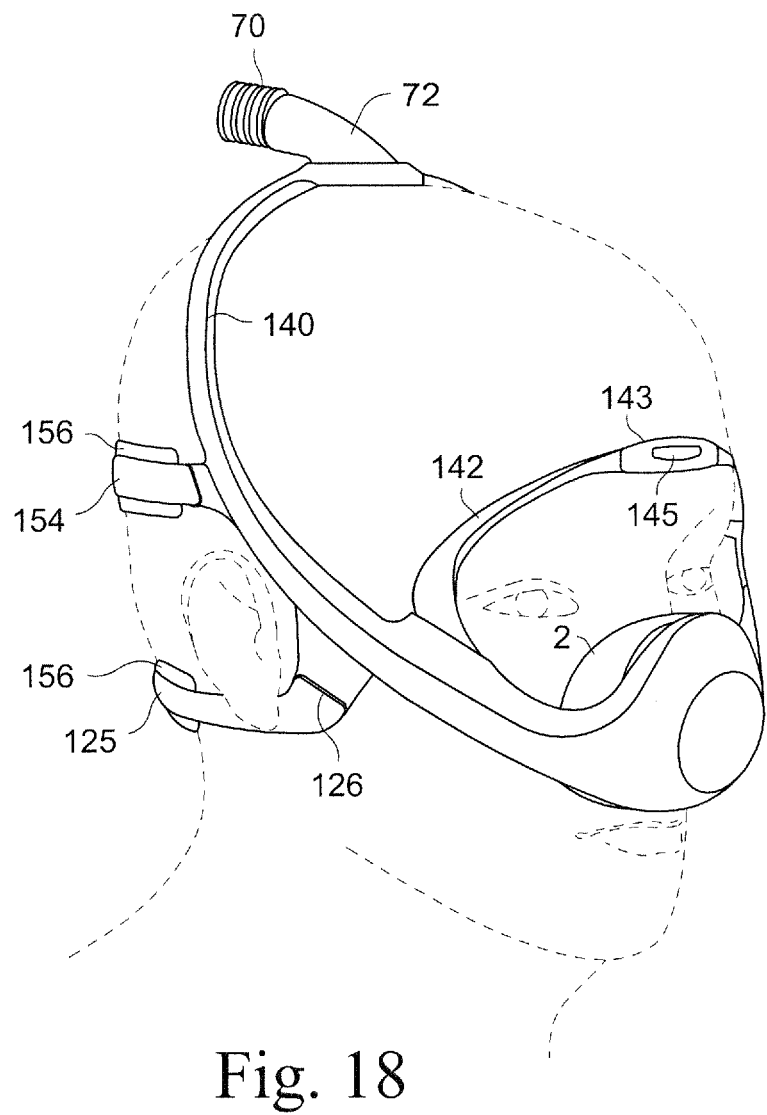
FIG. 18 schematically illustrates a patient interface and headgear system according to a sample embodiment of the present invention.

In another sample embodiment shown in FIG. 18, an integrated airflow and frame support 140 supports a patient interface 2. The patient interface may be, for example, a silicone cushion. A lower back strap 152 and an upper back strap 154 may be connected to the frame support 140. The lower strap 152 is configured to extend under the ears of the patient. The straps 152 and 154 may include padding 156 to provide strap support and improve the patient's comfort. The frame support 140 may include a stabilizing element 142 that extends across the forehead of the patient to stabilize the sealing contact of the patient interface 2 with the face of the patient. The stabilizing element 142 may include a forehead stabilizing element 143. A light, for example an LED, 145 may be integrated into the stabilizing element 142. A flow of breathable gas is delivered by a conduit 70 to a hose pivot which is provided on top of the frame support 140. The frame support may be configured as a hose, conduit, or tube to deliver the flow of pressurized breathable gas from the hose 70 to the patient interface 2.

The patient interface and headgear systems described above with respect to the sample embodiments of the present invention provide advantages over current patient interface and headgear systems. The patient interface and headgear systems of the sample embodiments are less obtrusive and more stable than currently available systems. The sample embodiments also provide stability to the patient interface without the use of forehead pads and other supports which may obstruct the vision of the patient.

The headgear described above also maintain their shape when not worn by the patient. The headgear may thus be removed from a container, e.g. a box, and will present the correct shape for application to the patient's head.

As another advantage, the patient interface and headgear system of the sample embodiments may be worn without the patient interface, e.g. the mask and/or cushion. The patient may temporarily remove the mask and/or cushion when the patient needs to do anything that requires removal of the mask and/or cushion. The mask and/or cushion may be quickly put back into position and a seal may be formed without the need for further adjustments of the headgear. As another example, if a patient were to wake up during the night and desire a drink, the mask and/or cushion may be detached without removing the headgear, or the headgear and the mask and/or cushion may be easily removed.

The headgear and frames described above may also be styled to include appropriate "masculine" and "feminine" characteristics. The headgear and frames also are easier to wear without distorting the patient's hair, which improves the aesthetics of the system while it is being worn and used by the patient.

The frame and the main body that supports the cushion can be obtained as one single piece by thermoforming a plastic sheet. The process can be more efficient compared to injection molding that would require high clamping forces for a mould of such planar dimensions. Alternatively, the frame can be thermoformed separately from the main body for the cushion. The thermoforming may be quicker and simpler than forming as a single piece. The shell can be injection molded and the two components can be connected with a snap-fit. This solution increases the part count but makes the thermoforming process less demanding and allows increased flexibility for the user since he/she will be able to slip on and off the entire mask or just take off the shell/cushion while still wearing the headgear/frame. The soft padding may be glued to the frame. There are a number of different possibilities according to the chosen style and the manufacturing complexity. These choices will influence cost. For example, in the sample embodiments including an elastic strap, the elastic strap can be efficiently nested during the cut process. That ensures a good level of material efficiency.

An alternative solution would be to cut two strips: one incorporating the padding for the yokes and the top strap and another incorporating the forehead padding. The two strips can be glued to the frame. The process involves handling of an additional component but greatly decreases the scrap.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. Also, the various embodiments described above may be implemented in conjunction with other embodiments, e.g., aspects of one embodiment may be combined with aspects of another embodiment to realize yet other embodiments. Further, each independent feature or component of any given assembly may constitute an additional embodiment. Furthermore, each individual component of any given assembly, one or more portions of an individual component of any given assembly, and various combinations of components from one or more embodiments may include one or more ornamental design features. In addition, while the invention has particular application to patients who suffer from OSA, it is to be appreciated that patients who suffer from other illnesses (e.g., congestive heart failure, diabetes, morbid obesity, stroke, barriatric surgery, etc.) can derive benefit from the above teachings. Moreover, the above teachings have applicability with patients and non-patients alike in non-medical applications.

What is claimed is:

1. A respiratory mask assembly for delivering a flow of breathable gas to a patient, the respiratory mask assembly comprising:
a structure comprising a plurality of rigidly connected elements, the structure being configured to contact a) at least one point on the patient's forehead, b) two points on the patient's temples, the two temple points being on opposite sides of the patient's face, and c) two points on the patient's cheek, the two cheek points being on opposite sides of the patient's face,
wherein one of the rigidly connected elements of the structure comprises a frame configured to support a cushion in contact with the patient's face, and another rigidly connected element of the structure comprises a rigid member adapted to extend across the forehead of the patient; and
a plurality of straps connected to the structure and configured to hold the structure against the at least one forehead point, the two temple points, and the two cheek points in a fully constrained manner without the presence of a mask cushion or nasal pillows or prongs,
wherein the rigidly connected elements of the structure form a rigid closed loop.

2. A respiratory mask assembly according to claim 1, wherein the structure comprises two yokes, each yoke being configured to contact one temple point and one cheek point.

3. A respiratory mask assembly according to claim 2, wherein the rigid member is configured to contact the at least one forehead point.

4. A respiratory mask assembly according to claim 3, wherein the two yokes, the rigid member and the cushion form the rigid closed loop.

5. A respiratory mask assembly according to claim 4, wherein the rigid member extends from one of the two yokes to the other of the two yokes.

6. A respiratory mask assembly according to claim 5, wherein the plurality of straps are connected to the pair of yokes.

7. A respiratory mask assembly according to claim 6, wherein the pair of yokes support the frame.

8. A respiratory mask assembly according to claim 7, wherein each yoke has a first end and a second end, the rigid member being connected to the first ends of the yokes and the frame being connected to second ends of the yokes.

9. A respiratory mask assembly according to claim 8, wherein the rigid member and the pair of yokes are integral to each other.

10. A respiratory mask assembly according to claim 8, wherein the rigid member and the pair of yokes are removably connected to each other.

11. A respiratory mask assembly according to claim 3, wherein the rigid member is rigid across its width yet flexible along its length.

12. A respiratory mask assembly according to claim 11, wherein the rigid member is configured to extend laterally across the patient's face.

13. A respiratory mask assembly according to claim 12, wherein the rigid member is configured to extend from the at least one forehead point to the patient interface.

14. A respiratory mask assembly according to claim 1, wherein the plurality of straps comprises at least one back strap configured to extend around the back of the patient's head.

15. A respiratory mask assembly according to claim 14, wherein the at least one back strap comprises a lower back strap and an upper back strap.

16. A respiratory mask assembly according to claim 1, wherein at least one of the plurality of straps comprises a top strap configured to extend over the top of the patient's head.

17. A respiratory mask assembly according to claim 16, wherein the top strap is configured to extend laterally across the patient's head.

18. A respiratory mask assembly according to claim 16, wherein the top strap is configured to extend across the patient's head from front to back.

19. A respiratory mask assembly according to claim 18, wherein the top strap is Y-shaped.

20. A respiratory mask assembly according to claim 1, wherein the plurality of straps comprise at least one back strap and at least one top strap that are integrally formed with the structure.

21. A respiratory mask assembly according to claim 1, wherein the plurality of straps comprise at least one back strap and at least one top strap that are releasably attachable to the structure.

22. A respiratory mask assembly according to claim 21, wherein the at least one back strap and the at least one top strap are adjustable with respect to the structure.

23. A respiratory mask assembly according to claim 1, wherein the plurality of straps comprise at least one back strap and at least one top strap that are integrally formed.

24. A respiratory mask assembly according to claim 1, wherein the structure is configured to contact two points on the patient's forehead.

25. A respiratory mask assembly according to claim 24, wherein positions of the two forehead contact points are adjustable.

26. A respiratory mask assembly according to claim 1, wherein the structure is configured as a conduit to deliver the flow of breathable gas to the patient interface.

27. A respiratory mask assembly according to claim 1, wherein the frame comprises at least one aperture to connect a conduit to deliver the flow of breathable gas to the cushion.

28. A respiratory mask assembly according to claim 1, further comprising padding attached to the structure and configured to contact the patient's face.

29. A respiratory mask assembly according to claim 28, wherein the padding comprises at least one of the straps.

30. A respiratory mask assembly according to claim 28, wherein the padding comprises thermoplastic elastomer or silicone rubber overmolded on the structure.

31. A respiratory mask assembly according to claim 1, further comprising padding attached to at least one of the plurality of straps and configured to contact the patient's head.

32. A respiratory mask assembly according to claim 31, wherein the padding comprises thermoplastic elastomer or silicone rubber overmolded to the straps.

33. A respiratory mask assembly according to claim 1, wherein the structure comprises a light at the least one forehead contact point.

34. A respiratory mask assembly according to claim 33, wherein the structure comprises a printed circuit board configured to support the light.

35. A respiratory mask assembly according to claim 1, wherein the frame and the structure are integrally formed by thermoforming a plastic sheet.

36. A respiratory mask assembly according to claim 1, wherein the frame is formed by a thermoforming process, the structure is formed by injection molding, and the frame and the structure are connected by a snap-fit.

37. A respiratory mask assembly according to claim 1, wherein the cushion comprises a nasal cushion, a full face cushion, nasal prongs, nasal pillows, or cannulae.

38. A respiratory mask assembly according to claim 1, wherein the rigid member is rigid in a first direction and flexible in a second direction.

39. A respiratory mask assembly according to claim 1, wherein the rigid loop is structured to be flexed by a moment around an axis extending from a superior portion of a patient's head to an inferior portion of a patient's head.

40. A respiratory mask assembly according to claim 39, wherein the rigid loop is structured to be flexed only by the moment around the axis.

41. A respiratory mask assembly according to claim 39, wherein the axis extends in a direction that is substantially perpendicular to a direction in which the rigid member extends.

42. A respiratory mask assembly for supporting a patient interface for delivering a flow of breathable gas to a patient, the respiratory mask assembly comprising:

a main body configured to support a patient interface in contact with the patient's face, the main body and the patient interface being configured to form a rigid closed loop; and a support adjustably connected to the main body and configured to engage the back of the patient's head, wherein the main body comprises a pair of yokes, a frame and a rigid member adapted to extend across the forehead of the patient, and wherein the rigid member connects the pair of yokes at a first end of the main body and the frame connects the yokes at a second end of the main body.

43. A respiratory mask assembly according to claim 42, wherein the patient interface comprises a nasal cushion, a full face cushion, nasal prongs, nasal pillows, or cannulae.

44. A respiratory mask assembly according to claim 42, wherein the rigid closed loop extends across the patient's temples, the patient's forehead and the patient's cheeks.

45. A respiratory mask assembly according to claim 42, wherein the frame is removably attached to the patient interface.

46. A respiratory mask assembly according to claim 45, wherein the support comprises at least one back strap and at least one top strap.

47. A respiratory mask assembly according to claim 46, wherein the support is integrally formed with the main body.

48. A respiratory mask assembly according to claim 46, wherein the support is releasably attachable to the main body.

49. A respiratory mask assembly according to claim 42, wherein the rigid member is rigid in a first direction and flexible in a second direction.

50. A respiratory mask assembly according to claim 42, wherein the rigid loop is structured to be flexed by a moment around an axis extending from a superior portion of a patient's head to an inferior portion of a patient's head.

51. A respiratory mask assembly according to claim 50, wherein the rigid loop is structured to be flexed only by the moment around the axis.

52. A respiratory mask assembly according to claim 51, wherein the axis extends in a direction that is substantially perpendicular to a direction in which the rigid member extends.

53. A respiratory mask assembly for delivering a flow of breathable gas to a patient, the respiratory mask assembly comprising:

a first yoke configured to contact a first temple point and a first cheek point;

a second yoke configured to contact a second temple point and a second cheek point; and a rigid member that extends across the forehead of the patient from the first temple point to the second temple point, wherein the first and second yokes are configured to support a patient interface in contact with the patient's face, and the first yoke, the second yoke, the rigid member and the patient interface form a rigid closed loop that extends across the patient's temples, the patient's forehead and the patient's cheeks.

54. A respiratory mask assembly according to claim 53, wherein the patient interface comprises a nasal cushion, a full face cushion, nasal prongs, nasal pillows, or cannulae.

55. A respiratory mask assembly according to claim 53, wherein the patient interface comprises a cushion removably attached to a frame.

56. A respiratory mask assembly according to claim 55, wherein each of the first and second yokes have a first end attached to the frame and a second end attached to the rigid member.

57. A respiratory mask assembly according to claim 56, further comprising a plurality of straps connected to the first and second yokes.

58. A respiratory mask assembly according to claim 57, wherein the plurality of straps includes at least one back strap and at least one top strap.

59. A respiratory mask assembly according to claim 58, wherein the plurality of straps are integrally formed with the first and second yokes.

60. A respiratory mask assembly according to claim 58, wherein the plurality of straps are releasably attachable to the first and second yokes.

61. A respiratory mask assembly according to claim 53, wherein the rigid member is rigid in a first direction and flexible in a second direction.

62. A respiratory mask assembly according to claim 53, wherein the rigid loop is structured to be flexed by a moment around an axis extending from a superior portion of a patient's head to an inferior portion of a patient's head.

63. A respiratory mask assembly according to claim 62, wherein the rigid loop is structured to be flexed only by the moment around the axis.

64. A respiratory mask assembly according to claim 63, wherein the axis extends in a direction that is substantially perpendicular to a direction in which the rigid member extends.

* * * * *